United States Patent
Xie et al.

(10) Patent No.: US 11,123,333 B2
(45) Date of Patent: Sep. 21, 2021

(54) INHIBITORS OF INTRACELLULAR INVASION

(71) Applicants: Meharry Medical College, Nashville, TN (US); Duke University, Durham, NC (US)

(72) Inventors: Hua Xie, Nashville, TN (US); Chin-Ho Chen, Durham, NC (US)

(73) Assignees: Meharry Medical College, Nashville, TN (US); Duke University, Durham, NC (US)

( * ) Notice: Subject to any disclaimer, the term of this patent is extended or adjusted under 35 U.S.C. 154(b) by 30 days.

(21) Appl. No.: 16/278,126

(22) Filed: Feb. 17, 2019

(65) Prior Publication Data

US 2019/0175565 A1 Jun. 13, 2019

Related U.S. Application Data

(63) Continuation of application No. PCT/US2017/047677, filed on Aug. 18, 2017.

(60) Provisional application No. 62/376,756, filed on Aug. 18, 2016.

(51) Int. Cl.
| | |
|---|---|
| A61K 31/439 | (2006.01) |
| A61K 31/166 | (2006.01) |
| A61P 31/04 | (2006.01) |
| C12Q 1/18 | (2006.01) |
| A61P 1/02 | (2006.01) |
| A61K 31/4748 | (2006.01) |
| A61K 8/02 | (2006.01) |
| A61K 8/04 | (2006.01) |
| A61K 8/42 | (2006.01) |
| A61K 8/49 | (2006.01) |
| A61Q 11/00 | (2006.01) |
| G01N 33/50 | (2006.01) |

(52) U.S. Cl.
CPC .......... *A61K 31/439* (2013.01); *A61K 8/0204* (2013.01); *A61K 8/042* (2013.01); *A61K 8/42* (2013.01); *A61K 8/4926* (2013.01); *A61K 31/166* (2013.01); *A61K 31/4748* (2013.01); *A61P 1/02* (2018.01); *A61P 31/04* (2018.01); *A61Q 11/00* (2013.01); *C12Q 1/18* (2013.01); *G01N 33/5044* (2013.01)

(58) Field of Classification Search
None
See application file for complete search history.

(56) References Cited

FOREIGN PATENT DOCUMENTS

| CN | 105770999 | | 7/2016 |
|---|---|---|---|
| CN | 105770999 A | * | 7/2016 |
| JP | 2014047157 | | 3/2014 |
| KR | 2014/0086704 | | 7/2014 |

OTHER PUBLICATIONS

How et al (Frontiers in Microbiology, 2016, 7(53), 1-14. (Year: 2016).*
The Mayo Clinic (Jan. 31, 2020; https://www.mayoclinic.org/diseases-conditions/hiv-aids/symptoms-causes/syc-20373524) (Year: 2020).*
Fuentes et al (Oct. 31, 2018; https://kidshealth.org/en/parents/treatments-prevent-premature-birth.html) (Year: 2018).*
Zelman et al (Feb. 13, 2018; https://www.webmd.com/rheumatoid-arthritis/rheumatoid-arthritis-prevention) (Year: 2018).*
Rogers et al (May 31, 2016; https://www.healthline.com/health/asthma-prevention#lung-testing) (Year: 2016).*
Lamont, RJ et al. Life below the gum line: pathogenic mechanisms of Porphyromonas gingivalis, Microbiology and Molecular Biology Reviews, 1998, p. 1244-1263, vol. 62, No. 4.
Kulp, A et al., Biological functions and biogenesis of secreted bacterial outer membrane vesicles, Annual Review of Microbiology, 2010, p. 163-184, vol. 64.
Ximenez-Fyvie, LA et al., Comparison of the microbiota of supra- and subgingival plaque in health and periodontitis., Journal of Clinical Periodontology, 2000, p. 648-657, vol. 27, No. 9.
Hajishengallis, G et al., The keystone-pathogen hypothesis, Nature Reviews Microbiology, 2012, p. 717-725, vol. 10.
Hajishengallis, G et al. Low-abundance biofilm species orchestrates inflammatory periodontal disease through the commensal microbiota and complement. Cell Host Microbe, 2011, p. 497-506, vol. 10.
Zenobia, C et al., Porphyromonas gingivalis virulence factors involved in subversion of leukocytes and microbial dysbiosis, Virulence, 2015, p. 236-243, vol. 6, No. 3.
Lamont, RJ et al., Subgingival colonization by Porphyromonas gingivalis., Oral Microbiology and Immunology, 2000, p. 341-349, vol. 15, No. 6.
Kolenbrander, PE, Oral microbial communities: biofilms, interactions, and genetic systems., Annual Review of Microbiology, 2000, p. 413-437, vol. 54.
Lamont, RJ et al. In or out: the invasiveness of oral bacteria., Periodontology 2000, 2002, p. 61-69, vol. 30.
Deshpande, RG et al, Invasion of aortic and heart endothelial cells by Porphyromonas gingivalis, Infection and Immunity, 1998, p. 5337-5343, vol. 66, No. 11.
Chaudhuri, S et al., Identification of a diguanylate cyclase. and its role in Porphyromonas gingivalis virulence, Infection and Immunity, 2014, p. 2728-2735, vol. 82, No. 7.
Yilmaz, O et al. Involvement of integrins in fimbriae-mediated binding and invasion by Porphyromonas gingivalis, Cellular Microbiology, 2002, p. 305-314, vol. 4, No. 5.
Dorn, BR et al., A Invasion of vascular cells in vitro by Porphyromonas endodontalis, International Endodontic Journal, 2002, p. 366-371, vol. 35, No. 4.
Li, L et al., Intracellular survival and vascular cell-to-cell transmission of Porphyromonas gingivalis, BMC Microbiology, 2008, p. 26, vol. 8.

(Continued)

*Primary Examiner* — Celeste A Roney
(74) *Attorney, Agent, or Firm* — Bradley Arant Boult Cummings; Timothy L. Capria; Alexandra C. Lynn

(57) ABSTRACT

The disclosure provides compounds that inhibit the invasion of host cells by intracellular parasites. These find use, for example, in treating and preventing periodontitis or a periodontitis-related condition or symptom.

18 Claims, 6 Drawing Sheets

(56) References Cited

OTHER PUBLICATIONS

Madianos, PN et al., Porphyromonas gingivalis FDC381 multiplies and persists within human oral epithelial cells in vitro, Infection and Immunity, 1996, p. 660-664, vol. 64, No. 2.
Tribble, GD et al. Bacterial invasion of epithelial cells and spreading in periodontal tissue. Periodontology 2000, 2010, p. 68-83, vol. 54, No. 1.
Amar, S et al., Is Porphyromonas gingivalis cell invasion required for atherogenesis? Pharmacotherapeutic Implications, 2009, Journal of Immunology, p. 1584-1592, vol. 182, No. 3.
Ho, MH et al., Functional Advantages of Porphyromonas gingivalis Vesicles. PLoS One, 2015, vol. 10, No. 4, e0123448.
Mantri, CK et al., Fimbriae-mediated outer membrane vesicle production and invasion of Porphyromonas gingivalis, MicrobiologyOpen, 2015, p. 53-65, vol. 4, No. 1.
Nakagawa, I et al., Inhibitory effects of Porphyromonas gingivalis fimbriae on interactions between extracellular matrix proteins and cellular integrins, Microbes and Infection, 2005, p. 157-163, vol. 7, No. 2.
Yilmaz, O et al., Gingival epithelial cell signalling and cytoskeletal responses to Porphyromonas gingivalis invasion, Microbiology, 2003, p. 2417-2426, vol. 149, No. 9.
Lamont, RJ et al., Porphyromonas gingivalis invasion of gingival epithelial cells, Infection and Immunity, 1995, p. 3878-3885, vol. 63, No. 10.
Dang, Z et al., Identification and synthesis of quinolizidines with anti-influenza a virus activity. ACS Medicinal Chemistry Letters, 2014, p. 942-946, vol. 5, No. 8.
Wang, H et al., Aloperine executes antitumor effects against multiple myeloma through dual apoptotic mechanisms, Journal of Hematology & Oncology, 2015, p. 26, vol. 8, No. 1.
Zhou, CC et al., Anti-inflammatory and anti-allergic action of aloperine, Acta Pharmacologica Sinica, 1989, p. 360-365, vol. 10, No. 4.
Chu, VC et al., Influenza virus entry and infection require host cell N-linked glycoprotein, Proceedings of the National Academy of Sciences USA, 2004, p. 18153-18158, vol. 101, No. 52.
Macia, E et al., Dynasore, a cell-permeable inhibitor of dynamin, Developmental Cell, 2006, p. 839-850, vol. 10, No. 6.
Furuta, N et al., Porphyromonas gingivalis outer membrane vesicles enter human epithelial cells via an endocytic pathway and are sorted to lysosomal compartments, Infection and Immunity, 2009, p. 4187-4196, vol. 77, No. 10.
Killoy, WJ, The clinical significance of local chemotherapies, Journal of Clinical Periodontology, 2002, p. 22-29, vol. 29, Suppl 2.
Mues, MB et al., Dynasore disrupts trafficking of herpes simplex virus proteins, Journal of Virology, 2015, p. 6673-6684, vol. 89, No. 13.
Thompson, HM et al., Dynamin 2 binds gamma-tubulin and participates in centrosome cohesion, Nature Cell Biology, 2004, p. 335-342, vol. 6, No. 4.
Yoshida, S et al., Exploiting host microtubule dynamics: a new aspect of bacterial invasion, Trends in Microbiology, 2003, p. 139-143, vol. 11, No. 3.
Takeuchi, H et al., Cell entry and exit by periodontal pathogen via recycling pathway, Communicative & Integrative Biology, 2011, p. 587-589, vol. 4, No. 5.
Robinson, MS, Forty Years of Clathrin-coated Vesicles, Traffic, 2015, p. 1210-1238, vol. 16, No. 12.
Lin, WC et al., Five bitter compounds display different anti-inflammatory effects through modulating cytokine secretion using mouse primary splenocytes in vitro, Journal of Agricultural and Food Chemistry, 2011, p. 184-192, vol. 59, No. 1.
Boisvert, H et al., Clathrin-dependent entry of a gingipain adhesin peptide and Porphyromonas gingivalis into host cells, Cell Microbiology, 2008, p. 2538-2552, vol. 10, No. 12.
Takeuchi, H et al., Exit of intracellular Porphyromonas gingivalis from gingival epithelial cells is mediated by endocytic recycling pathway, Cell Microbiology, 2011, p. 677-691, vol. 13.
Belton, CM et al., Fluorescence image analysis of the association between Porphyromonas gingivalis and gingival epithelial cells, Cell Microbiology, 1999, p. 215-223, vol. 1, No. 1.
Danino, D et al., Rapid constriction of lipid bilayers by the mechanochemical enzyme dynamin, Journal of Structural Biology, 2004, p. 259-267, vol. 147, No. 3.
Abazeed, ME et al., Cell-free transport from the trans-golgi network to late endosome requires factors involved in formation and consumption of clathrin-coated vesicles, Journal of Biological Chemistry, 2005, p. 4442-4450, vol. 280, No. 6.
Hunstad, DA et al., Intracellular lifestyles and immune evasion strategies of uropathogenic *Escherichia coli*, Annual Review of Microbiology, 2010, p. 203-221, vol. 64, No. 1.
Foster, TJ et al., Adhesion, invasion and evasion: the many functions of the surface proteins of *Staphylococcus aureus*, Nature Reviews Microbiology, 2014, p. 49-62, vol. 12, No. 1.
Tribble, GD et al., A Porphyromonas gingivalis haloacid dehalogenase family phosphatase interacts with human phosphoproteins and is important for invasion, Proceedings of the National Academy of Sciences USA, 2006, p. 11027-11032, vol. 103, No. 23.
Moffatt, CE et al., Porphyromonas gingivalis SerB-mediated dephosphorylation of host cell cofilin modulates invasion efficiency, Cellular Microbiology, 2012, p. 577-588, vol. 14, No. 4.
Radhakrishnan, GK et al., Modulation of host microtubule dynamics by pathogenic bacteria, BioMolecular Concepts, 2012, p. 571-580, vol. 3, No. 6.
Macdonald, IA et al., Stress-induced outer membrane vesicle production by Pseudomonas.aeruginosa, Journal of Bacteriology, 2013, p. 2971-2981, vol. 195, No. 13.
The International Search Report and the Written Opinion of the International Searching Authority of PCT/US2017/047677, dated Jan. 18, 2018.

\* cited by examiner

INHIBITORS OF INTRACELLULAR INVASION

CROSS-REFERENCE TO RELATED APPLICATIONS

This application is a continuation of and cites the priority of PCT/US17/47677 filed 18 Aug. 2017, which is currently pending, and cites the priority of U.S. 62/376,756 filed 18 Aug. 2016. The contents of PCT/US17/47677 and U.S. 62/376,756 are incorporated herein by reference in their entireties.

STATEMENT REGARDING FEDERALLY SPONSORED RESEARCH OR DEVELOPMENT

This invention was made with government support under grant numbers DE022428 and 025332 (HX) awarded by NIDCR; grant number R01AI065310 awarded by NIAID; grant numbers MD007593 and MD007586 awarded by NIMHD; and grant numbers UL1 RR024975 and UL1 TR000445 awarded by NCATS. The government has certain rights in the invention.

In this context "government" refers to the government of the United States of America.

BACKGROUND

A. Field of the Disclosure

The present disclosure relates generally to methods of treatment and/or prevention of diseases and medical conditions, and specifically to those diseases and medical conditions that are associated with or characterized by periodontal disease.

B. Background

Poor oral health is strongly associated with several more serious health conditions. These include diverse conditions such as periodontitis, atherosclerosis, human immunodeficiency virus (HIV) disease, tooth loss, coronary artery disease, stroke, premature birth (in infants born to mothers with poor oral health), low birth weight (in infants born to mothers with poor oral health), diabetes, respiratory problems, rheumatoid arthritis, and asthma. It is believed that inflammation caused by periodontal disease may be responsible for the association. Therefore it may be possible to prevent these conditions by treating or preventing the underlying periodontal disease.

Periodontal disease is often initiated by host cell invasion by an intracellular parasite. One prominent such intracellular parasite is the bacterium *Porphyromonas gingivalis*. It is found in the oral cavity, as well as in the upper gastrointestinal tract, the respiratory tract, and the colon. It has also been isolated from women with bacterial vaginosis. Collagen degradation observed in chronic periodontal disease results in part from the collagenase enzymes of this species. It has been shown in an in vitro study that *P. gingivalis* can invade human gingival fibroblasts and can survive in them in the presence of considerable concentrations of antibiotics. *P. gingivalis* also invades gingival epithelial cells in high numbers, in which cases both bacteria and epithelial cells survive for extended periods of time. High levels of specific antibodies can be detected in patients harboring *P. gingivalis*.

*P. gingivalis* has been associated not only with periodontal disease, but also with HIV infection.

Although oral transmission of HIV-1 is relatively rare, it may occur during breast feeding in infants and during oro-genital contact in adults. In addition, studies of animal models indicate that oral HIV transmission can occur in macaques and humanized mice after non-traumatic oral exposure to cell-free SIV or HIV, respectively. In general, epithelial surfaces present the first line of defense against pathogens such as bacteria and viruses, however HIV-1 appears to be able to penetrate and be transmitted across a multi-layered epithelium in the absence of any apparent breach or lesion. Several mechanisms have been proposed to explain how HIV-1 gains access to permissive cells across mucosal surfaces. Although evidence of HIV-1 entry into epithelial cells is accumulating, the mechanism is not understood. Multiple alternative receptors, other than CD4, CCR5, and CXCR4, seem to be involved. For instance, gp340 on the cell surfaces of female genital tract epithelial cells, DEC-205 on renal epithelial cells, and CCR5 on oral keratinocytes may mediate HIV-1 entry into these cells.

*P. gingivalis* promotes HIV-1 entry of epithelial cells. Studies have shown an increased infection of the pretreated epithelial cells with R5-type, but not with X4 type HIV-1. Epithelial cell entry of HIV-1, both R5 and X4 types, mediated by *P. gingivalis* appears to be positively correlated with invasive activity of the *P. gingivalis* strains.

However, *P. gingivalis* infection is difficult to prevent and treat.

SUMMARY

The disclosure provides compounds that inhibit the invasion of host cells by intracellular parasites. These find use, for example, in treating, reducing the likelihood prior to onset, or reducing the severity prior to onset of periodontitis or a periodontitis-related condition or symptom.

In a first aspect, a pharmaceutical composition for treating or preventing periodontitis or a periodontitis-related condition or symptom is provided, the composition comprising a compound selected from the group consisting of: an inhibitor of vesical formation, an inhibitor of endocytosis, and an inhibitor of dynamin; and wherein the pharmaceutical composition is formulated for local delivery to the gingival tissue.

In a second aspect, a method of treating or preventing periodontitis or a periodontitis-related condition or symptom in a subject is provided, the method comprising locally administering to the gingival tissue of the subject a therapeutically effective amount of a compound selected from the group consisting of an inhibitor of vesical formation, an inhibitor of endocytosis, and an inhibitor of dynamin.

In a third aspect, a use of a compound in the manufacture of a pharmaceutical composition for treating or preventing periodontitis or a periodontitis-related condition or symptom is provided, wherein the compound is selected from the group consisting of: an inhibitor of vesical formation, an inhibitor of endocytosis, and an inhibitor of dynamin.

In a fourth aspect, a method of reducing the likelihood of the invasion of a host cell by an intracellular parasite is provided, the method comprising contacting the host cell with an effective concentration of a compound selected from the group consisting of: an inhibitor of vesical formation, an inhibitor of endocytosis, and an inhibitor of dynamin.

In a fifth aspect, a method of screening a candidate factor for activity in treating or preventing periodontitis or a periodontitis-related condition or symptom, the method comprising exposing a plurality of gingival tissue cells to the candidate factor in the presence of an intracellular parasite; and measuring the rate of infection of the plurality of oral epithelial cells by the intracellular parasite.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

BRIEF DESCRIPTION OF THE DRAWINGS

(FIG. 1A) *P. gingivalis* vesicles were stained with anti-33277 serum and a secondary antibody conjugated with Alex Fluor 546 (red), nuclei were stained with DAPI (blue), and HOKs were visualized with confocal microscopy. Scale bar, 20 μm. (FIG. 1B) After treatment with Alop1 or dynasore, the number of HOKs carrying intercellular *P. gingivalis* vesicles (infection rate) was determined by counting the infected HOKs in 30 random areas. Each bar represents the percentage of HOKs with intercellular vesicles. The SDs are indicated (n=3). An asterisk indicates the statistical significance of invasive rates between *P. gingivalis* vesicles in the presence or absence of compounds ($P<0.05$; t test).

(FIG. 2A) HOKs treated with 30 μM of different compounds including DMSO, Alop1, dynasore, cytochalasin D, and nocodazole for 2 h. *P. gingivalis* vesicles were stained with anti-33277 serum and a secondary antibody conjugated with Alex Fluor 546 (red), nuclei were stained with DAPI (blue), and HOKs were visualized with confocal microscopy. Scale bar, 20 μm. (FIG. 2B) Infection rate and level (average of fluorescence intensity in each cell) of HOKs treated with different compounds are presented and compared with a DMSO control. Means and SDs are indicated (n=3). An asterisk indicates the statistical significance of invasive rates and levels between *P. gingivalis* vesicles ($P<0.05$; t test).

(FIG. 3A) Inhibition of *P. gingivalis* invasion by different compounds. HOK nuclei were stained with DAPI (blue), and internalized *P. gingivalis* cells were stained with primary anti-33277 serum and a secondary antibody conjugated with Alex Fluor 546 (red) and visualized with confocal microscopy. Scale bars, 20 μm. (FIG. 3B) Each bar represents relative *P. gingivalis* infection rate or level of HOKs treated with compounds compared to that of untreated HOKs. An asterisk indicates the statistical significance between invasive rates or levels between *P. gingivalis* cells in the presence or absence of compounds ($P<0.05$; t test).

(FIG. 6B) Each bar represents average of fluorescence intensity (red) in 100 infected cells cultured with Alop11 or dynasore relative to that without compounds.

(FIG. 7A) Comparison of the growth curves of *P. gingivalis* 33277 in the presence of compounds. Cells were grown in TSB media in the presence or absence of Alop1 or dynasore (30 μM). Shown in the curves are means of four samples, with error bars representing SEM. One ml aliquots were taken and the OD600 was measured over a period of 44 hr. (FIG. 7B) Gene expression in *P. gingivalis* in the presence or absence of Alop1 or dynasore (30 μM) was determined using qRT-PCR analysis. Expression levels were normalized with 16s rRNA. Representative data are shown as means with standard deviation of three biological replicates and relative to expression level of the housekeeping gene glk.

DETAILED DESCRIPTION

A. Definitions

Figure 1A:
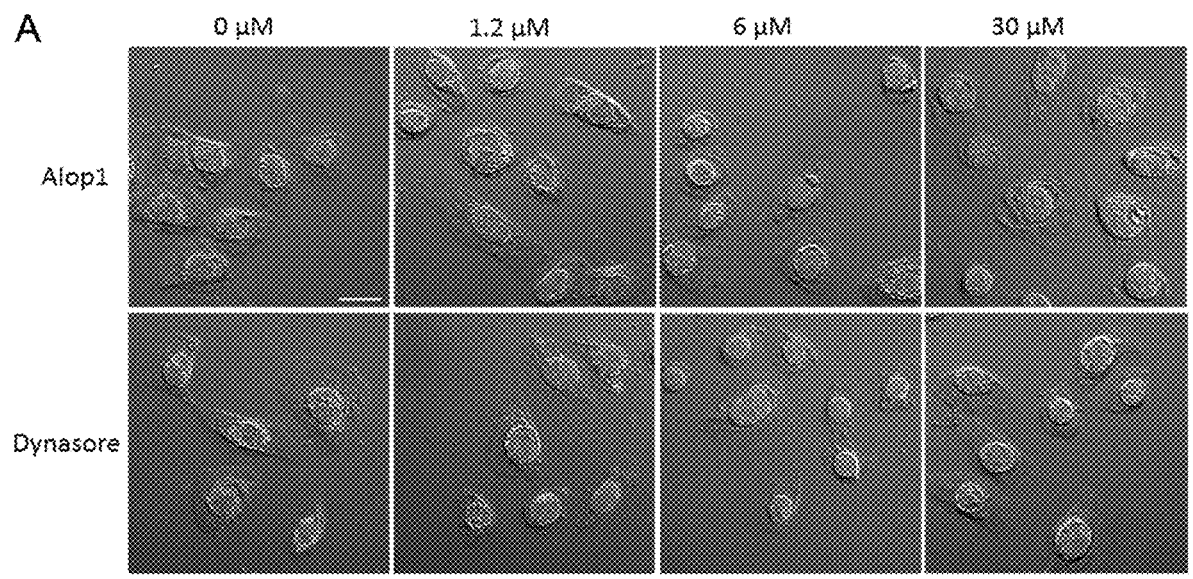
FIGS. 1A and 1B. Invasive activity of *P. gingivalis* vesicles into HOKs in the presence of different doses of Alop1 and dynasore for 2 h.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

The terminology used herein is for the purpose of describing particular embodiments only and is not intended to be limiting. As used herein, the singular forms "a", "an" and "the" are intended to include the plural forms as well, unless the context clearly indicates otherwise.

The terms "first", "second", and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

The term "consisting essentially of" means that, in addition to the recited elements, what is claimed may also contain other elements (steps, structures, ingredients, components, etc.) that do not adversely affect the operability of what is claimed for its intended purpose as stated in this disclosure. Importantly, this term excludes such other elements that adversely affect the operability of what is claimed for its intended purpose as stated in this disclosure, even if such other elements might enhance the operability of what is claimed for some other purpose.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. For biological systems, the term "about" refers to an acceptable standard deviation of error, preferably not more than 2-fold of a given value. Numerical quantities given herein are approximate unless stated otherwise, meaning that the term "about" or "approximately" can be inferred when not expressly stated.

Terms such as "administering" or "administration" include acts such as prescribing, dispensing, giving, or taking a substance such that what is prescribed, dispensed, given, or taken actually contacts the patient's body externally or internally (or both). In embodiments of this disclosure, terms such as "administering" or "administration" include self-administering, self-administration, and the like, of a substance. Indeed, it is specifically contemplated that instructions or a prescription by a medical professional to a subject or patient to take or otherwise self-administer a substance is an act of administration.

The terms "prevention", "prevent", "preventing", "suppression", "suppress" and "suppressing" as used herein refer to a course of action (such as administering a pharmaceutical composition) initiated prior to the onset of a clinical manifestation of a disease state or condition so as to reduce the likelihood or severity. Such reduction in likelihood or severity need not be absolute to be useful.

The terms "treatment", "treat" and "treating" as used herein refers a course of action (such as administering a pharmaceutical composition) initiated after the onset of a clinical manifestation of a disease state or condition so as to eliminate or reduce such clinical manifestation of the disease state or condition. Such treating need not be absolute to be useful.

The term "in need of treatment" as used herein refers to a judgment made by a caregiver that a patient requires or will benefit from treatment. This judgment is made based on a variety of factors that are in the realm of a caregiver's expertise, but that include the knowledge that the patient is ill, or will be ill, as the result of a condition that is treatable by a method or device of the present disclosure.

The term "in need of prevention" as used herein refers to a judgment made by a caregiver that a patient requires or will benefit from prevention. This judgment is made based on a variety of factors that are in the realm of a caregiver's expertise, but that include the knowledge that the patient will be ill or may become ill, as the result of a condition that is preventable by a method or device of the disclosure.

The term "individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

The term "therapeutically effective amount" as used herein refers to an amount of a compound, either alone or as a part of a pharmaceutical composition, that is capable of having any detectable, positive effect on any symptom, aspect, or characteristics of a disease state or condition. Such effect need not be absolute to be beneficial.

The term "prodrug" as used herein includes functional derivatives of a disclosed compound which are readily convertible in vivo into the required compound. Thus, in the methods of treatment of the present disclosure, the term "administering" shall encompass the treatment of the various disease states/conditions described with the compound specifically disclosed or with a prodrug which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

The term "pharmaceutically acceptable salts" as used herein includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

B. Compounds

The present disclosure provides compounds that inhibit the invasion of host cells by intracellular parasites. Such compounds may have downstream effects of treating and preventing periodontitis or a periodontitis-related condition or symptom in a subject. Specifically, it has been discovered that host cell invasion can be inhibited using classes of compounds that include inhibitors of vesical formation, inhibitors of endocytosis, and inhibitors of dynamin. Such compounds are referred to herein as "active compounds."

The active compounds reduce one or more of vesical formation, endocytosis, and dynamin activity, either directly or through upregulation of expression, either in vitro or in vivo. The present disclosure also provides compounds that indirectly decrease such activity by either stimulating the activity of a molecule that decreases the activity or by inhibiting the activity of a molecule that increases the activity.

A specific example of an active compound is dynasore. Dynasore is a GTPase inhibitor that rapidly and reversibly inhibits dynamin activity, which prevents endocytosis and clathrin-dependent vesicle formation. However, comparison between cells treated with dynasore and RNA interference of genes encoding dynamin, reveals evidence that dynasore reduces labile cholesterol in the plasma membrane, and disrupts lipid raft organization, in a dynamin-independent manner having the following structure:

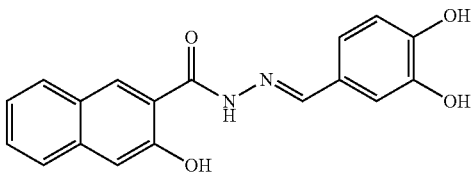 [SMILES: O=C(N/N=C/c1ccc(O)c(O)c1)c1cc2ccccc2cc1O]

Dynasore monohydrate salt is commercially available (for example, from Sigma Aldrich). As explained in more detail in the working examples below, dynasore has been observed to inhibit host cell invasion by *P. gingivalis* at concentrations of 1.2, 6, and 30 µM in vitro.

Another specific example of an active compound is aloperine (Alop 1). A loperine is a quinolizidine-type lupine alkaloid found in *Sophora* species. It seems to be an inhibitor of endocytosis. It is commercially available (for example, from Sigma Aldrich) having the following structure:

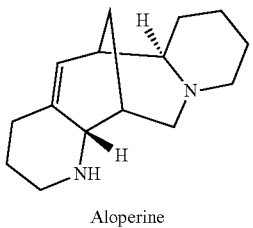 [SMILES: C1=C2CCCN[C@H]2C2CC1[C@H]1CCCCN1C2]

Aloperine

As explained in more detail in the working examples below, aloperine has been observed to inhibit host cell invasion by *P. gingivalis* at concentrations of 6 and 30 µM in vitro.

Unless stated otherwise, all active compounds are to be construed as including a metabolite; such a metabolite may be formed either in vivo within the body or as a result of biochemical activity in vitro. It is within the scope of this disclosure than any active compound may be limited to a non-metabolite compound.

C. Pharmaceutical Compositions

In a general embodiment, the active compound is in the form of a pharmaceutical composition. The compositions disclosed may comprise one or more of such active compounds, in combination with a pharmaceutically acceptable carrier. Examples of such carriers and methods of formulation may be found in Remington: The Science and Practice of Pharmacy (20th Ed., Lippincott, Williams & Wilkins, Daniel Limmer, editor), and are generally well understood by those skilled in the art. To form a pharmaceutically acceptable composition suitable for administration, such compositions will contain a therapeutically effective amount of an active compound.

The pharmaceutical compositions of the disclosure may be used in the treatment and prevention methods of the present disclosure. Such compositions are administered to a subject in amounts sufficient to deliver a therapeutically effective amount of the active compound so as to be effective in the treatment and prevention methods disclosed herein.

The therapeutically effective amount may vary according to a variety of factors such as the subject's condition, weight, sex and age. For example, some embodiments of the composition comprise up to the median lethal dose (LD50) of the active compound. The LD50 can be ascertained using standard toxicological methods, or by reference to past studies. For example, the intraperitoneal LD50 (mouse) for aloperine has been observed to be 154 mg/kg; the intravenous LD50 (rabbit and mouse) for aloperine has been observed to be 75 mg/kg; the oral LD50 (mouse) for aloperine has been observed to be 869 mg/kg; and the oral LD50 (rat) for aloperine has been observed to be 480 mg/kg (see "LookChem: Aloperine" website available at http://www-.lookchem.com/Aloperine/(last visited 26 Jul. 2016)).

Alternatively, the pharmaceutical composition may be formulated to achieve a desired concentration of the active compound in the gingival tissue of the subject. In some embodiments of the composition, the composition contains an amount of active agent sufficient to achieve a concentration of at least 12 nM active agent in the gingival tissue of a subject. In some embodiments of the composition, the composition contains an amount of active agent sufficient to achieve a concentration of at least 120 nM active agent in the gingival tissue of a subject. In some embodiments of the composition, the composition contains an amount of active agent sufficient to achieve a concentration of at least 1.2 µM active agent in the gingival tissue of a subject. In specific embodiments, the composition contains an amount of active agent sufficient to achieve a concentration of at least one of 6 and 30 µM in the gingival tissue of a subject. In a specific embodiment of the pharmaceutical composition, the composition contains an amount of dynasore sufficient to achieve a concentration of at least 12 nM, at least 120 nM, at least 1.2 µM, at least 6 µM, or at least 30 µM in the gingival tissue. In another specific embodiment, of the pharmaceutical composition, the composition contains an amount of aloperine sufficient to achieve a concentration of at least 60 nM, at least 600 nM, at least 6 µM, or at least 30 µM in the gingival tissue.

Other factors include the mode and site of administration. The pharmaceutical compositions may be formulated to be provided to the subject in any method known in the art. Exemplary dosage forms include subcutaneous, intravenous, topical, epicutaneous, oral, intraosseous, intramuscular, intranasal and pulmonary. The compositions of the present disclosure may be formulated to be administered only once to the subject or more than once to the subject. Furthermore, when the compositions are administered to the subject more than once, a variety of regimens may be used, such as once per day, once per week, once per month or once per year. The compositions may also be formulated to be administered to the subject more than one time per day. The therapeutically effective amount of the active compound and appropriate dosing regimens may be identified by testing in order to obtain optimal activity, while minimizing any potential side effects. In addition, formulation for co-administration or sequential administration of other agents may be desirable.

The compositions of the present disclosure may be formulated to be administered systemically, such as by intravenous administration, or locally such as by subcutaneous injection or by application of a gel, fiber, paste or cream.

The compositions of the present disclosure may further comprise agents which improve the solubility, half-life, absorption, etc. of the active compound. Furthermore, the compositions of the present disclosure may further comprise agents that attenuate undesirable side effects and/or decrease the toxicity of the active compound. Examples of such agents are described in a variety of texts, such as Remington: The Science and Practice of Pharmacy (20th Ed., Lippincott, Williams & Wilkins, Daniel Limmer, editor).

The compositions of the present disclosure can be formulated in a wide variety of dosage forms for administration. For example, the compositions can be in the form of tablets, capsules, sachets, lozenges, troches, pills, powders, granules, elixirs, tinctures, solutions, suspensions, syrups, ointments, creams, pastes, emulsions, or solutions for intravenous administration or injection. Other dosage forms include for administration transdermally, via patch mechanism or ointment. Further dosage forms include formulations suitable for delivery by nebulizers or metered dose inhalers. Any of the foregoing may be modified to provide for timed release and/or sustained release formulations.

In the present disclosure, the pharmaceutical compositions may further comprise a pharmaceutically acceptable carrier. Such carriers may include vehicles, adjuvants, surfactants, suspending agents, emulsifying agents, inert fillers, diluents, excipients, wetting agents, binders, lubricants, buffering agents, disintegrating agents and carriers, as well as accessory agents, such as coloring agents and flavoring agents (collectively referred to herein as a carrier). Typically, the pharmaceutically acceptable carrier is chemically inert to the active compounds and has no detrimental side effects or toxicity under the conditions of use. The pharmaceutically acceptable carriers can include polymers and polymer matrices. The nature of the pharmaceutically acceptable carrier may differ depending on the particular dosage form employed and other characteristics of the composition.

For instance, compositions for oral administration in solid form, such as tablets, capsules, sachets, lozenges, troches, pills, powders, or granules, the active compound may be combined with an oral, non-toxic pharmaceutically acceptable inert carrier, such as inert fillers, suitable binders, lubricants, disintegrating agents and accessory agents. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, and the like. Disintegrators include, without limitation, starch, methyl cellulose, agar, bentonite, xanthum gum and the like. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid as well as the other carriers described herein. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, and gels containing, in addition to the active ingredient, such carriers as are known in the art.

The pharmaceutical composition may be a dentifrice. Dentifrices have the advantage of being widely available to consumers. People are therefore familiar with the use of dentifrices, and in most societies apply a dentifrice at least once daily as part of an oral hygiene regime. In addition, dentifrices are effective for the local delivery of active compounds to salivary glands.

The dentifrice may be selected from a group consisting of a paste, a gel, a mouthwash, a powder, and a tooth soap. In some embodiments of the composition, the dentifrice is a paste or gel comprising at least one of an abrasive, a surfactant, a humectant, and a thickener. Such abrasives include hydrated silica, dicalcium phosphate dihydrate, calcium carbonate, sodium bicarbonate, calcium pyrophosphate, and alumina. Such surfactants include sodium lauryl sulfate, sodium N-lauryl sarcosinate, pluronics, sodium lauryl sulfoacetate. Such anticaries agents include fluoride. Such tartar control ingredients include tetrasodium pyrophosphate, Gantrez S-70, sodium tripolyphosphate, and methyl vinyl ether/maleic anhydride copolymer. The dentifrice may further comprise one or more of: water; pH buffers; humectants (to prevent dry-out and increase pleasant mouth feel) such as, glycerin, sorbitol, polypropylene glycol, xylitol, and polyethylene glycol; thickeners such as silica thickeners, sodium aluminum silicates, and clays; gums such as sodium carboxymethyl cellulose, cellulose ethers, xantham gum, carrageenans, sodium alginate, and carbopols; antibacterial agents; flavoring agents such as, water-insoluble essential oils; sweetening agents such as, saccharin, dextrose, levulose, cyclamate, aspartate; coloring agents; and binders to provide consistency and shape.

For oral administration by mouthwash, the active compound may be combined with one or more of: water and alcohol (such as ethyl alcohol). The mouthwash may further comprise one or more of: surfactants, tartar control ingredients, anticaries agents, buffers, humectants, antibacterial agents, flavoring agents, and coloring agents as described in the preceding section In a specific embodiment, the dentifrice is a powder comprising any of the abrasives described above. The powder may further comprise any of the dry components provided above as suitable in a toothpaste. In another specific embodiment, the dentifrice is a tooth soap comprising one or more of oil and water. The oil may be any that is known to be suitable in a tooth soap, such as olive oil, coconut oil, an essential oil, and peppermint oil.

The pharmaceutical composition may be a chewing gum. The gum may comprise the active compound and a gum, such as butadiene-based synthetic rubber, birch bark tar, chicle, mastic gum, spruce gum, paraffin wax, tolu resin, styrene-butadiene rubber, isobutylene, isoprene copolymer, and petroleum wax. The gum will be present at a concentration sufficient to confer the requisite chewiness to the chewing gum, as could be formulated by one skilled in the art. Flavorings may be added, including those listed above.

In addition to dentifrice and gum forms of the composition, oral liquid forms, such as tinctures, solutions, suspensions, elixirs and syrups, the molecules of the present disclosure can be dissolved in diluents, such as water, saline, or alcohols. Furthermore, the oral liquid forms may comprise suitably flavored suspending or dispersing agents such as synthetic and natural gums, for example, tragacanth, acacia, methylcellulose and the like. Moreover, when desired or necessary, suitable coloring agents or other accessory agents can also be incorporated into the mixture. Other dispersing agents that may be employed include glycerin and the like.

Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and non-aqueous sterile suspensions that can include suspending agents, solubilizers, thickening agents, stabilizers, and preservatives. The compound(s) may be administered in a physiologically acceptable diluent, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap, an oil or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations and in the dentifrice, include petroleum, animal, vegetable, or synthetic oils. Specific examples of oils include peanut, soybean, sesame, cottonseed, corn, olive, petrolatum, and mineral. Suitable fatty acids for use in parenteral formulations include polyethylene sorbitan fatty acid esters, such as sorbitan monooleate and the high molecular weight adducts of ethylene oxide with a hydrophobic base, formed by the condensation of propylene oxide with propylene glycol, oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include: (a) cationic detergents such as, for example, dimethyldialkylammonium halides, and alkylpyridinium halides; (b) anionic detergents such as, for example, alkyl, aryl, and olefin sulfonates, alkyl, olefin, ether, and monoglyceride sulfates, and sulfosuccinates; (c) nonionic detergents such as, for example, fatty amine oxides, fatty acid alkanolamides, and polyoxyethylene polypropylene copolymers; (d) amphoteric detergents such as, for example, alkylbeta-aminopropionates, and 2-alkylimidazoline quaternary ammonium salts; and (e) mixtures thereof.

Suitable preservatives and buffers can be used in such formulations. In order to minimize or eliminate irritation at the site of injection, such compositions may contain one or more nonionic surfactants having a hydrophile-lipophile balance (HLB) of from about 12 to about 17.

Topical dosage forms, such as ointments, creams, pastes, and emulsions, containing the active compound, can be admixed with a variety of carrier materials well known in the art, such as, e.g., alcohols, aloe vera gel, allantoin, glycerine, vitamin A and E oils, mineral oil, PPG2 myristyl propionate, and the like, to form alcoholic solutions, topical cleansers, cleansing creams, skin gels, skin lotions, and shampoos in cream or gel formulations. Inclusion of a skin exfoliant or dermal abrasive preparation may also be used. Such topical preparations may be applied to a patch, bandage or dressing for transdermal delivery, or may be applied to a bandage or dressing for delivery directly to the site of a wound or cutaneous injury.

The active compounds of the present disclosure can also be formulated to be administered in the form of liposome delivery systems, such as small unilamellar vesicles, large unilamellar vesicles and antiemtrics. Liposomes can be formed from a variety of phospholipids, such as cholesterol, stearylamine or phosphatidylcholines. Such liposomes may also contain monoclonal antibodies to direct delivery of the liposome to a particular cell type or group of cell types.

The active compounds of the present disclosure may also be coupled with soluble polymers as targetable drug carriers. Such polymers can include polyvinyl-pyrrolidone, pyran copolymer, polyhydroxypropylmethacryl-amidephenol, polyhydroxyethylaspartamidephenol, or polyethyl-eneoxidepolylysine substituted with palmitoyl residues. Furthermore, the active compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

D. Methods of Treatment and Prevention

The present disclosure provides a method of treatment and/or prevention of a disease or medical condition associated with or characterized by periodontitis in a subject in need thereof, the method comprising administering any of the active compounds or pharmaceutical compositions disclosed above to the subject in a therapeutically effective amount. Such active compound may be for example: an inhibitor of vesical formation, an inhibitor of endocytosis, and an inhibitor of dynamin. Specific examples of such active compounds are dynasore and aloperine. Conditions associated with or characterized by periodontitis include periodontitis, atherosclerosis, human immunodeficiency virus (HIV) disease, tooth loss, coronary artery disease, stroke, premature birth, low birth weight, poorly controlled diabetes, respiratory problems, rheumatoid arthritis, and asthma. Furthermore, some medical treatments are associated with xerostomia, which can lead to periodontitis. Such medical treatments include, but are not limited to anticholinergic drugs, drugs with sympathomimetic actions, local radiation, and chemotherapy. Anticholinergic drugs that may give rise to xerostomia include, but are not limited to atropine and analogs (antimuscarinics), tricyclic antidepressants, serotonin reuptake inhibitors, antihistamines, antiemetics, and antipsychotics. Drugs with sympathomimetic actions associated with xerostomia include, but are not limited to decongestants, bronchodilators, appetite suppressants, and amphetamines. Other treatments that are also associated with xerostomia include, but are not limited to lithium, omeprazole, oxybutynin, disopyramide, dideoxyinosine, didanosine, diuretics, and protease inhibitors. In some embodiments of the method the subject has undergone or is currently undergoing a medical treatment associated with xerostomia, including but not limited to any of the treatments described above. A further embodiment of the method comprises co-administering a treatment associated with at least one of xerostomia and periodontitis to the subject, including but not limited to any of the treatments described above.

The method of treatment and/or prevention comprises administering to the subject the active compound in an amount sufficient to treat or prevent periodontitis or a periodontitis-related condition or symptom (therapeutically effective amount). The method will often further comprise identifying a subject in need of such treatment or prevention. Too little active compound would fail to provide the therapeutic effect. On the other hand, excessive active compound could lead to undesired side-effects.

The therapeutically effective amount may vary according to a variety of factors such as the subject's condition, weight, sex and age. For example, some embodiments of the method comprise administration of up to the median lethal dose (LD50) of the active compound. The LD50 can be ascertained using standard toxicological methods, or by reference to past studies. For example, the intraperitoneal LD50 (mouse) for aloperine has been observed to be 154 mg/kg; the intravenous LD50 (rabbit and mouse) for aloperine has been observed to be 75 mg/kg; the oral LD50 (mouse) for aloperine has been observed to be 869 mg/kg; and the oral LD50 (rat) for aloperine has been observed to be 480 mg/kg (see "LookChem: Aloperine" website available at http://www.lookchem.com/Aloperine/(last visited 26 Jul. 2016)).

Alternatively, the method may comprise delivering a desired concentration of the active compound to the gingival tissue of the subject. In some embodiments of the method, the desired concentration is at least one of 12 nM, 120 nM, and 1.2 µM. In specific embodiments, the desired concentration is at least one of 6 and 30 µM. In a specific embodiment of the method, the active compound is dynasore and the desired concentration is at least 12 nM, at least 120 nM, at least 1.2 µM, at least 6 µM, or at least 30 µM. In another specific embodiment of the method the active compound is aloperine, and the desired concentration is at least 60 nM, at least 600 nM, at least 6 µM, or at least 30 µM.

If, after the administration of the active compound, the subject still has periodontitis or a periodontitis-related condition or symptom, or is at risk for the same, then an optional step of the method is to continue administration of the active compound or pharmaceutical composition.

In one embodiment, the method comprises delivering the active compound to the gingival tissue of the subject. It is desirable to deliver the active compound to the gingival tissue because this is the site of intracellular invasion by numerous periodontal pathogens, such as *P. gingivalis*. The presence of the active compound in the gingival tissue is necessary to prevent invasion of the cells in this tissue. Targeted delivery to the gingival tissue could also prevent unwanted effects on other tissues or organs. In an alternate embodiment, the method comprises administering the active compound locally to the subject's mouth. It is desirable to administer the active compound to the subject's mouth because the gingival tissues are in the subject's mouth. A specific embodiment comprises administering the active compound locally to the subject's mouth in which the active compound is administered in a dentifrice or gum. A dentifrice or gum containing active compound would be useful to treat or prevent periodontitis or a periodontitis-related condition or symptom because these formulations might also contain additives to improve overall oral health (e.g., fluoride). Human subjects likely already use similar formulations for routine oral hygiene, so subjects would be more likely to comply with the treatment regimen, leading to better outcomes.

E. Methods of Prevention of Invasion of a Host Cell

A method of reducing the likelihood of the invasion of a host cell by an intracellular parasite is provided, the method comprising contacting the host cell with an effective concentration of any of the active compound discussed above. Contact may occur in vitro or in vivo. Intracellular parasites include bacteria, fungi, viruses, and protists. Numerous examples are known. *P. gingivalis* is discussed above. Other examples of bacteria include *Bartonella henselae, Francisella tularensis, Listeria monocytogenes, Salmonella typhi, Brucella* spp., *Legionella* spp., *Mycobacterium* spp., *Nocardia* spp., *Rhodococcus equi, Yersinia* spp., *Neisseria meningitidis, Chlamydia* spp., *Rickettsia* spp., and *Coxiella* spp. Examples of intracellular parasitic fungi include *Histoplasma capsulatum, Cryptococcus neoformans*, and *Pneumocystis jirovecii*. Protozoal examples include apicomplexans (e.g., *Babesia* spp., *Plasmodium* spp., *Cryptosporidium parvum, Cyclospora cayetanensis, Isospora belli*, and *Toxoplasma gondii*) and trypanosomatids. In some embodiments of the method the intracellular parasite is an oral pathogen, regardless of its taxon.

Consequently, the host cell may be any cell that is vulnerable to invasion by any of the foregoing organisms.

In some embodiments of the method, the host cell is selected from the group consisting of an oral epithelial cell, a gingival fibroblast, an aortic endothelial cell, a heart endothelial cell, and a vascular smooth muscle cell. Exemplary host cells include those from various mammalian species, including humans and domesticated animals. Such cells are known to be vulnerable to various intracellular parasites, including the aforementioned *P. gingivalis*. In more specific embodiments of the method, the host cell is a cell in the gingival tissue selected from the group consisting of an oral epithelial cell and a gingival fibroblast. In a further specific embodiment of the method, the host cell is an oral keratinocyte, such as an oral keratinocyte from a human or a domesticated animal.

The effective concentration is any concentration at which the active compound exerts a significant inhibitory effect on cellular invasion by the parasite. In some embodiments of the method, the effective concentration is at least one of 12 nM, 120 nM, and 1.2 µM. In specific embodiments, the effective concentration is at least one of 6 and 30 µM. In a specific embodiment of the method, the active compound is dynasore and the effective concentration is at least 12 nM, at least 120 nM, at least 1.2 µM, at least 6 µM, or at least 30 µM. In another specific embodiment of the method the active compound is aloperine, and the effective concentration is at least 60 nM, at least 600 nM, at least 6 µM, or at least 30 µM.

F. Methods of Screening

A method of screening a candidate factor for activity in treating or preventing periodontitis or a periodontitis-related condition or symptom is provided, the method comprising exposing a plurality of gingival tissue cells to the candidate factor in the presence of an intracellular parasite; and measuring the rate of infection of the plurality of oral epithelial cells by the intracellular parasite. The parasite and the oral epithelial cells may be any that are taught above as suitable in the method for reducing the likelihood of the invasion of a host cell by an intracellular parasite.

The candidate longevity factor may be any type of factor, including a physical factor, a chemical factor, a genetic factor, a biochemical factor, or an ecological factor. Examples of physical factors include temperature, oxidation potential, pressure, and radiation. Examples of chemical factors include osmotic potential, concentration of inorganic compounds, organic compounds, pH, and salinity. Examples of biochemical factors include a nutrient concentration, a prion, and a toxin concentration. Examples of ecological factors include population density, intrinsic rate of growth, carrying capacity, predation, parasitism, and growth rate. Examples of genetic factors include a genotype, a mutation, an episome, a transposable genetic element, a virus, and a viroid. However, as the purpose of the assay is to identify putative treatment or prevention factors that were previously unknown, it should be emphasized that the factor may be any factor to which the cell can be subjected.

The method of measuring the rate of infection may be any known in the art. In a specific embodiment of the method the rate of infection is measured by staining the mixture of cells and parasites and examining the stained mixture microscopically. Fluorescent dyes can be used for this purpose, to enhance the signal when viewed by epifluorescent microscopy. The use of fluorescent dyes also allows fluorometry to be used to measure the number of intracellular parasites present (for example, after separation of host cells from free parasites). In a specific embodiment, the rate of infection is measured by permeabilizing the host cells, immunostaining the sample with a fluorescent probe, acquiring confocal microscopic images of the immuno-stained sample, enumerating the total number of host cells by direct count, and enumerating the number of host cells harboring intracellular parasites by direct count. Such direct counting methods are well known in the art, and typically involve counting cells in a set number of microscopic fields and extrapolating the results to the entire sample. However, any approach to the direct count may be employed.

Some embodiments of the method are intended to screen specifically for factors that decrease the rate of parasitic invasion of the host cell, as opposed to factors that induce mortality of the parasite. In such embodiments the factor may be a non-antibiotic factor (i.e., a factor which is not necessarily toxic to the parasite). Such embodiments of the method may also involve counting the total number of parasites in the same after exposure to the factor, to differentiate between factors that have antibiotic activity and factors that have anti-invasive activity.

In some embodiments of the method, the gingival tissue cell is selected from the group consisting of an oral epithelial cell and a gingival fibroblast. Exemplary gingival tissue cells include those from various mammalian species, including humans and domesticated animals. In a further specific embodiment of the method, the host cell is an oral keratinocyte, such as an oral keratinocyte from a human or a domesticated animal.

Well known statistical methods may be used if necessary to detect a decrease in infection rate of a sample exposed to the factor relative to a benchmark value. The benchmark value may be established using a parallel control study, or may be obtained from the literature describing previous studies. However, in some instances such statistical methods may not be necessary due to obvious effects of the factor.

G. Examples

1. Example 1: Two Small Molecules Block Oral Epithelial Cell Invasion by *Porphyromons gingivalis*

*Porphyromonas gingivalis* is a keystone pathogen of periodontitis. One of its bacterial characteristics is the ability to invade various host cells, including nonphagocytic epithelial cells and fibroblasts, which is known to facilitate *P. gingivalis* adaptation and survival in the gingival environment. This study investigated two small compounds, Alop1 and dynasore, for their role in inhibition of *P. gingivalis* invasion. Confocal microscopy showed that these two compounds significantly reduced invasion of *P. gingivalis* and its outer membrane vesicles into human oral keratinocytes in a dose-dependent manner. The inhibitory effects of dynasore, a dynamin inhibitor, on the bacterial entry is consistent with the notion that *P. gingivalis* invasion is mediated by a clathrin-mediated endocytic machinery. It was also observed that microtubule arrangement, but not actin, was altered in the host cells treated with Alop1 or dynasore, suggesting an involvement of microtubule in this inhibitory activity. This work provides an opportunity to develop compounds against *P. gingivalis* infection.

Introduction

*Porphyromonas gingivalis* is a gram-negative bacterium strongly associated with chronic periodontitis[1-3]. Recently, a keystone pathogen hypothesis regarding the pathogenesis of periodontitis was proposed, suggesting that the presence of *P. gingivalis* in the oral cavity, even at low levels, is capable of disturbing host-microbial homeostasis and inducing periodontitis [3,4]. The pathogenicity of *P. gingivalis* has been extensively characterized, including its abilities to colonize the surfaces of oral tissues, interact with other oral bacteria, induce a destructive immune response, and invade host cells [5-8]. All of these virulence features have been attractive therapeutic targets for preventing *P. gingivalis* infection.

Cell invasion by *P. gingivalis* is found in oral epithelial cells, gingival fibroblasts, aortic and heart endothelial cells, and vascular smooth muscle cells [9-12]. More significantly, *P. gingivalis*, once internalized, can multiply and persist within host cells [13,14]. *P. gingivalis* invasion is believed to protect the bacteria against environmental challenges, including innate immune surveillance systems and antibiotic treatment [15], which likely plays a pivotal role in chronic bacterial infection. The ability of *P. gingivalis* to invade host cells also appears to be critical in the progression of atherosclerosis [16]. Recently, it was demonstrated that the outer membrane vesicles of *P. gingivalis* are also invasive and exhibit significantly higher invasion efficiency than their parental bacterial cells [17,18]. Studies of *P. gingivalis* invasion have provided insight into the mechanisms by which this organism invades non-phagocytic cells such as epithelial cells and fibroblasts. A number of bacterial proteins have been identified as ligands that interact with host receptors to initiate an internalization process. One of best known ligand/receptor interactions is the pair of FimA, a structural protein of the bacterial major fimbriae, and $\alpha 5\beta 1$ integrin on the surface of epithelial cells [11,19]. The consequence of the specific ligand/receptor recognition results in cytoskeletal remodeling, which promotes the engulfment of bacteria [11,20]. Involvement of the cytoskeleton in *P. gingivalis* invasion is further supported by evidence that cytochalasin D, an inhibitor of actin polymerization, and nocodazole, an inhibitor of microtubule formation, inhibited *P. gingivalis* invasion of epithelial cells [21]. However, the mechanism of actin and microtubule in the bacterial invasion is not clear.

Since control of *P. gingivalis* infection by targeting bacterial invasion activity is limited, it was attempted to identify inhibitory agents able to block *P. gingivalis* invasion. The focus was the lupine alkaloid, aloperine (Alop1), which is a known principal constituent of *Sophora* species used in traditional Chinese medicine against a variety of ailments [23,24]. Recently, it was demonstrated that Alop1 and its derivatives were effective against the H1N1 influenza A virus, although the mechanism of Alop1's action remains to be determined [22]. Based on the well-known fact that viral entry is involved in receptor-mediated endocytosis [25], it is proposed that Alop1 may also block the entry of *P. gingivalis* and its outer membrane vesicles (OMV) into primary oral keratinocytes. Another interesting endocytosis inhibitor is dynasore, a small compound first discovered by Macia et al. [26]. It is well-defined that dynasore specifically inhibits dynamin-mediated clathrin-coated vesicle formation during endocytosis.

Materials and Methods

Bacterial Strains and Vesicle Preparation and Quantification

*P. gingivalis* ATCC 33277 was grown from frozen stocks in trypticase soy broth (TSB) or on TSB blood agar plates supplemented with yeast extract (1 mg/ml), hemin (5 µg/ml), and menadione (1 µg/ml), and incubated at 37° C. in an anaerobic chamber (85% N2, 10% H2, 5% CO2). *P. gingivalis* vesicles were prepared as previously described [27]. Briefly, *P. gingivalis* was grown to the late exponential phase and growth media were collected by centrifugation at 10,000×g for 15 min at 4° C. and filtered through a 0.22 µm pore size filter (CellTreat) to remove residual bacteria. Vesicles were collected by ultracentrifugation at 126,000×g for 2 h at 4° C. and resuspended in phosphate-buffered saline (PBS) containing 10% glycerol. Since quantifying bacterial vesicles by their protein or lipid content in weight represents the most common way to normalize data [28], proteins were extracted from vesicles using a BugBuster1 Protein Extraction Reagent (Novagen). Protein concentrations were determined with a Bio-Rad Protein Assay Kit (Bio-Rad). To determine lipid content, *P. gingivalis* vesicles were resuspended in 100 µl sterile PBS and quantized using the fluorescent lipophilic dye FM4-64 (Molecular Probes). Fluorescence was measured at 506 nm (excitation) and 750 nm (emission) to obtain relative fluorescence units/ml [29].

Preparation of Compounds

Aloperine and nocodazole were purchased from Sigma-Aldrich. Alop1 denotes HPLC purified aloperine to ensure the purity of the compound is greater than 95%. Dynasore was purchased from Tocris Bioscience. Cytochalasin D was purchased from Invitrogen.

Treatment of Host Cells

Human oral keratinocytes (HOKs) were purchased from ScienCell Research Laboratories (Carlsbad, Calif.) and cultured in specific media, according to the manufacturer's instructions. Prior to treatment, HOKs ($2\times10^4$) were seeded and grown overnight in poly-L-lysine-coated 35 mm glass bottom dishes (MatTek Corporation) at 37° C., 5% CO2, then exposed to *P. gingivalis* 33277 ($2\times10^6$) or its vesicles (100 ng) for 0 or proper experimental times. To examine the role of Alop1 and dynasore in the bacterial invasion, the compounds were added to the medium 10 min prior to infection. The cytotoxicity of compound treatments was evaluated with a Pierce LDH Cytotoxicity Assay Kit (Thermo Scientific). There was no cytotoxicity detected under our experimental conditions.

Confocal Microscopy

HOKs were fixed with 3.8% formaldehyde in a sodium phosphate buffer at room temperature for 10 min after treatment, permeabilized with 0.1% Triton X-100 for 10 min, and blocked with 5% bovine serum albumin in PBS for 1 h. HOKs were then immunostained with pan-specific antibodies of *P. gingivalis* 33277, and α Tubulin or Actin mono-antibodies (Santa Cruz Biotechnology, Dallas, Tex.), followed by goat anti-rabbit IgG conjugated to Alex Fluor 546 (Invitrogen). Nuclei were stained with DAPI (Invitrogen). Confocal images were acquired using a Nikon A1R confocal microscope.

For infection rate determination, the number of HOKs with intercellular *P. gingivalis* cells or its vesicles were determined and divided by the total number of HOKs by counting the cells in 30 random areas (5.6 µm×5.6 µm) under the confocal microscope. Moreover, fluorescence intensity was determined in 100 individual cells using imaging software NIS-Elements AR 4.20, which reflects the level of intercellular *P. gingivalis* and its vesicles in the infected HOKs.

Exit of Intercellular *P. gingivalis* Cells Assay

HOKs grown in a 6-well plate were infected with *P. gingivalis* 33277 cells at multiplicity of infection (MOI) of 100 for 1 h. Extracellular bacteria were removed by washing three times with PBS. The infected HOKs were then trypsinized, seeded in a glass bottom dish, and cultured with fresh media for another 20 h. To eliminate *P. gingivalis* cells exiting from HOKs, the growth media were supplemented with gentamicin (300 µg/ml) and metronidazole (200 µg/ml). To visualize the remaining intercellular *P. gingivalis*, HOKs were fixed and subjected to immunostaining and confocal microscopy.

RNA Isolation and RT-PCR

*P. gingivalis* was grown anaerobically in TSB in the presence or absence of Alop1 and dynasore (30 µM) for 16 h. Bacteria were harvested by centrifugation and homogenized in Trizol Reagent (Invitrogen). The RNA in the supernatant was then purified using an RNeasy mini spin column (Qiagen, Valencia, Calif.). RNA samples were digested on the column with RNase-free DNase. Total RNA was tested using an Agilent 2100 Bioanalyzer to ensure the quality of the samples. RT-PCR analysis was performed by using an SsoAdvanced™ Universal SYBR1Green Supermix (Bio-Rad) on the CFX96 Touch™ Real-Time PCR Detection System (Bio-Rad) according to the manufacturer's instructions. Primers are listed in S1 Table. Amplification reactions consisted of a reverse transcription cycle at 42° C. for 30 min, an initial activation at 95° C. for 3 min, and 40 cycles of 95° C. for 15 s and 60° C. for 30 s. The expression levels of the investigated genes were determined by using the formula 2-ΔΔCt, where MCT (Cycle Threshold)=(CT [genes of test sample]-CT[16SrRNA of test sample])–(CT [genes of control sample]–CT[16SrRNA of control sample]).

Statistical Analyses

A student's t-test was used to determine statistical significance of the differences in the invasive activities of *P. gingivalis* cells and vesicles in the presence or absence of Alop1 or dynasore. A P<0.05 was considered significant. Values are shown ±SD unless stated otherwise.

Results

Figure 1B:
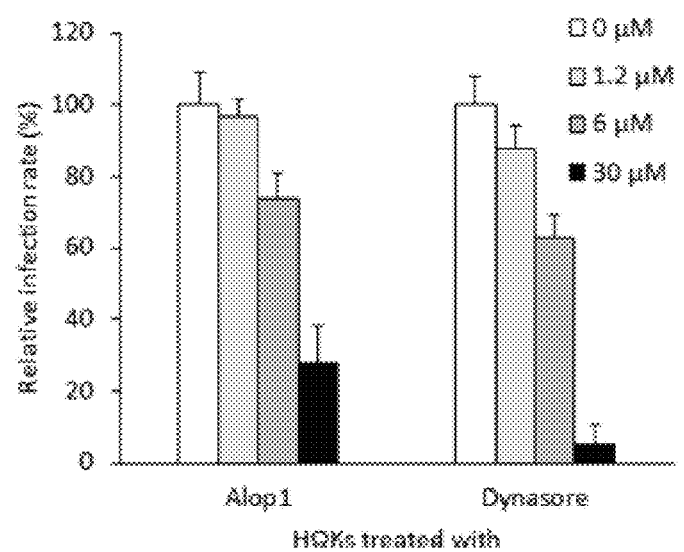
Figure 2A:
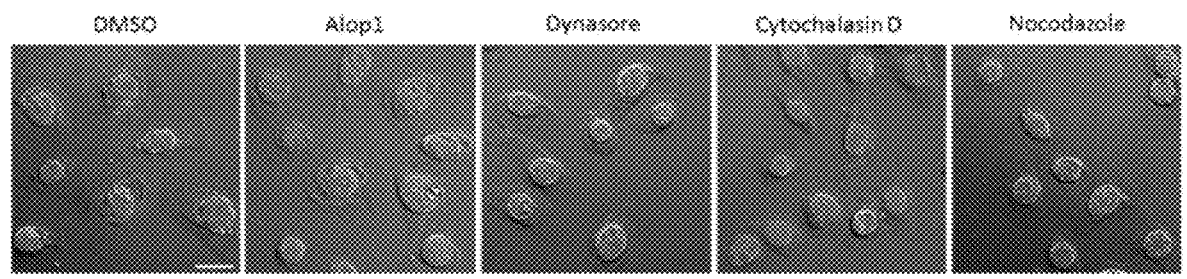
FIGS. 2A and 2B. Comparison of inhibitory activities of compounds in internalization of *P. gingivalis* vesicles.
Figure 2B:
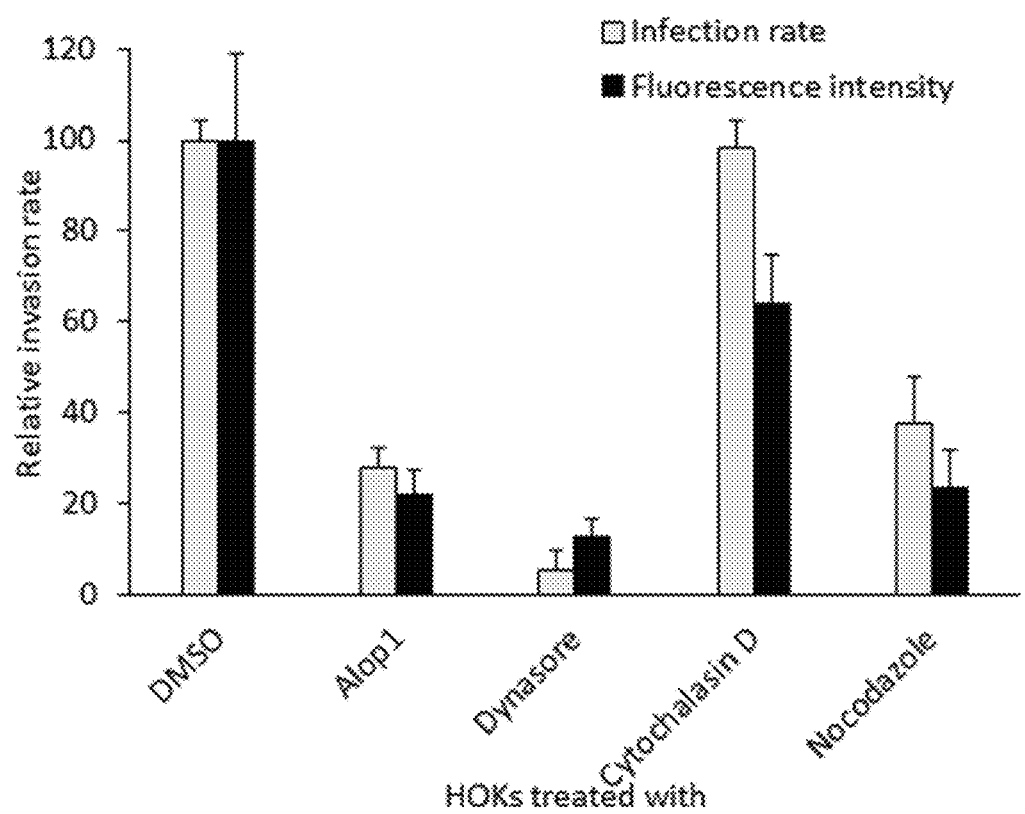
Figure 3A:
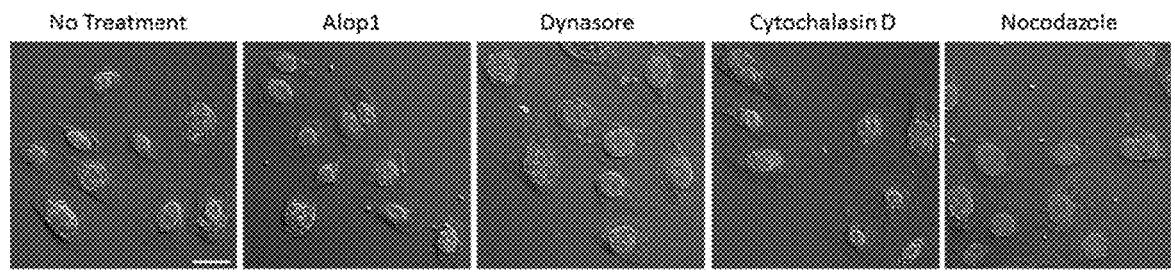
FIGS. 3A and 3B.
Figure 3B:
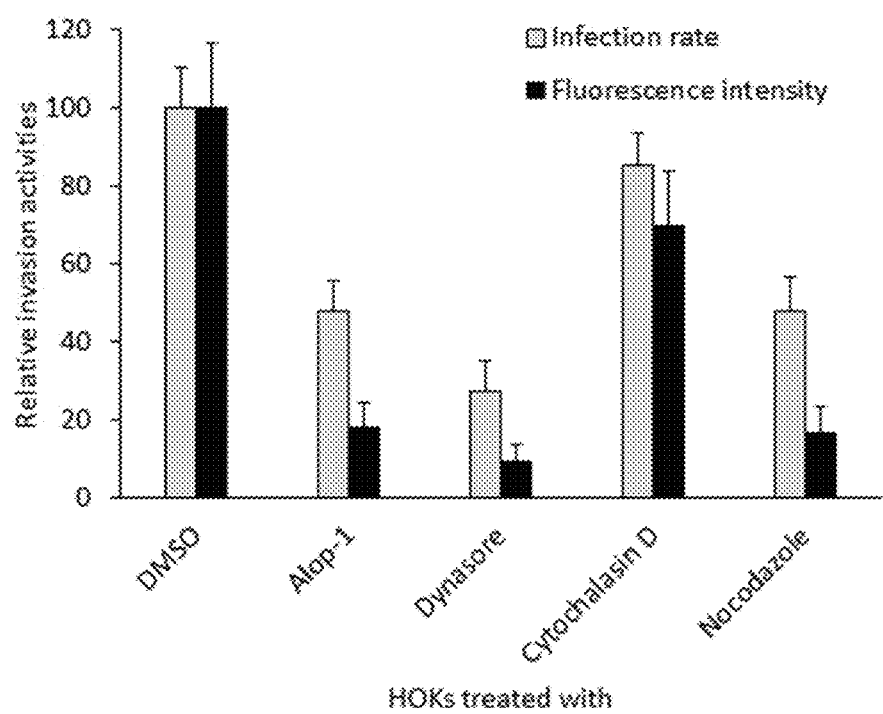

Inhibitory Activity and Efficiency of Alop1 and Dynasore Upon *P. gingivalis* Invasion Cumulating evidence has shown that both *P. gingivalis* and its OMVs are able to efficiently invade oral epithelial cells [8,15]. To search for compounds capable of blocking invasion of *P. gingivalis*, Alop1 and dynasore were tested for their role in the bacterial vesicle invasion using confocal microscopy. Both Alop1 and dynasore displayed an inhibitory activity on *P. gingivalis* vesicle invasion of HOKs in a dose-dependent manner (FIG. 1A). By counting 30 random areas (5.6 µm×5.6 µm), it was found that the number of HOKs with intracellular vesicles were significantly decreased in the presence of Alop1 and dynasore when compared to those observed in HOKs unexposed to the compounds. As shown in FIG. 1B, Alop1 reduced the total number of HOKs with intracellular vesicles about 66% at 30 µM, and 26% at 6 µM (P<0.001), and dynasore reduced the numbers by over 95% at 30 µM, and 40% at 6 µM (P<0.001). Furthermore, the internalized vesicles in the HOKs were quantified by intercellular fluorescence intensity with NIS-Elements AR 4.20 imaging software. After analysis of 100 infected HOKs with or without the compound treatment (30 µM), respectively, significantly lower fluorescence intensity was detected in HOKs exposed to Alop1 or dynasore compared to that in the non-exposed HOKs (FIG. 2). The effect of two well-known invasion inhibitors, cytochalasin D and nocodazole, was also tested. A similar inhibitory efficiency was found between Alop1 and nocodazole, while dynasore exhibited the highest efficiency. However, significant inhibitory activity was not observed in the presence of cytochalasin D, suggesting a microtubule-involved mechanism of inhibition. Similarly, Alop1, nocodazole, and dynasore were also found to effectively block *P. gingivalis* cell entry into HOKs (FIGS. 3A and 3B).

Microtubule-Associated *P. gingivalis* Invasion

Figure 4:
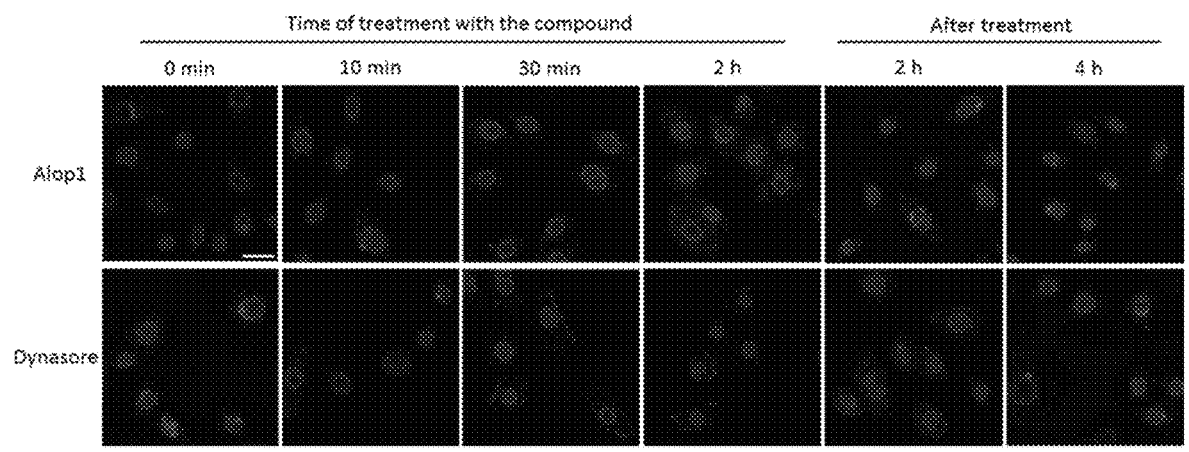
FIG. 4. Microtubule rearrangement in HOKs induced by Alop1 and dynasore. After treated with Alop1 (30 μM) or dynasore (30 μM) for 0, 10, 30 min, or 2 has well as recovery from treatment, HOKs were stained with anti-α-tubulin, anti-IgG with Alex Fluor 546 (red) and DAPI (blue) and visualized under a confocal microscope. Scale bar, 20 μm.
Figure 5:
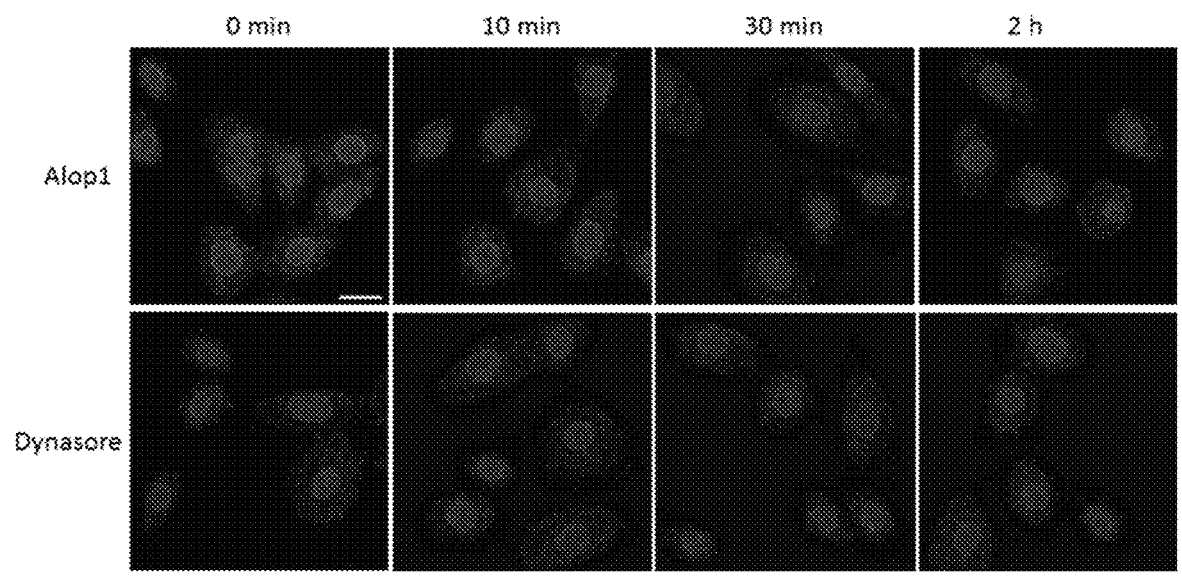
FIG. 5. Actin arrangement in HOKs treated with compounds. After treated with Alop1 or dynasore for 0, 10, 30 min, or 2 h, HOKs were stained with antiactin antibodies, anti-IgG with Alex Fluor 546 (red) and DAPI (blue) and visualized under a confocal microscope. Scale bar, 20 μm.

Rearrangements of host cytoskeleton have been observed during the course of bacterial infection [30]. This study examined if the HOK cytoskeleton is a target of Alop1 and dynasore for inhibition of *P. gingivalis* invasion. Differential rearrangements of microtubules were observed in the cells treated with 30 μMAlop1 or dynasore compared to that seen in the untreated cells. Confocal microscopy revealed nucleation of microtubules near the cell nucleus in the untreated HOKs (FIG. 4), consistent with previous observations [32]. Interestingly, treatment of Alop1 or dynasore each leads to a unique microtubule arrangement, which could be observed 30 min after the treatment (FIG. 4). In the cells exposed to Alop1, microtubules appeared diffuse in the cytoplasm, while microtubules became more condensed and formed a cortical outer shell at the cell membrane after the HOKs were treated with dynasore. It was demonstrated that the effects of Alop1 and dynasore were reversible, and recovery of differential microtubule arrangements started at 2 h after the compounds were removed from the growth media. In contrast, alteration of actin arrangement was not detected in the cells treated with Alop1 and dynasore (FIG. 5), suggesting that these compounds likely target microtubule arrangement involved in invasion of *P. gingivalis* cells and vesicles. Since the rearrangement patterns of microtubules induced by Alop1 or dynasore were significantly distinct, mechanisms of microtubule arrangements induced by these compounds may be different.

Dual Function of Dynasore

Figure 6A:
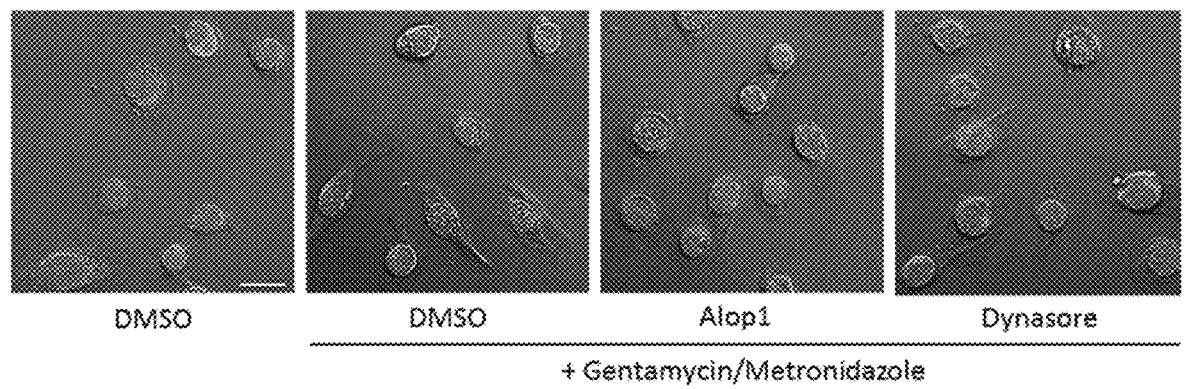
FIGS. 6A and 6B. Exit of intracellular *P. gingivalis* cells from HOKs. (6A) HOKs were cultured in the presence of antibiotics (gentamicin and metronidazole) as well as Alop1 and dynasore (30 μM) for 20 h after infection with *P. gingivalis* 33277. *P. gingivalis* cells were stained with anti-33277 serum and a secondary antibody conjugated with Alex Fluor 546 (red), nuclei were stained with DAPI (blue), and HOKs were visualized with confocal microscopy. Scale bar, 20 μm.
Figure 6B:
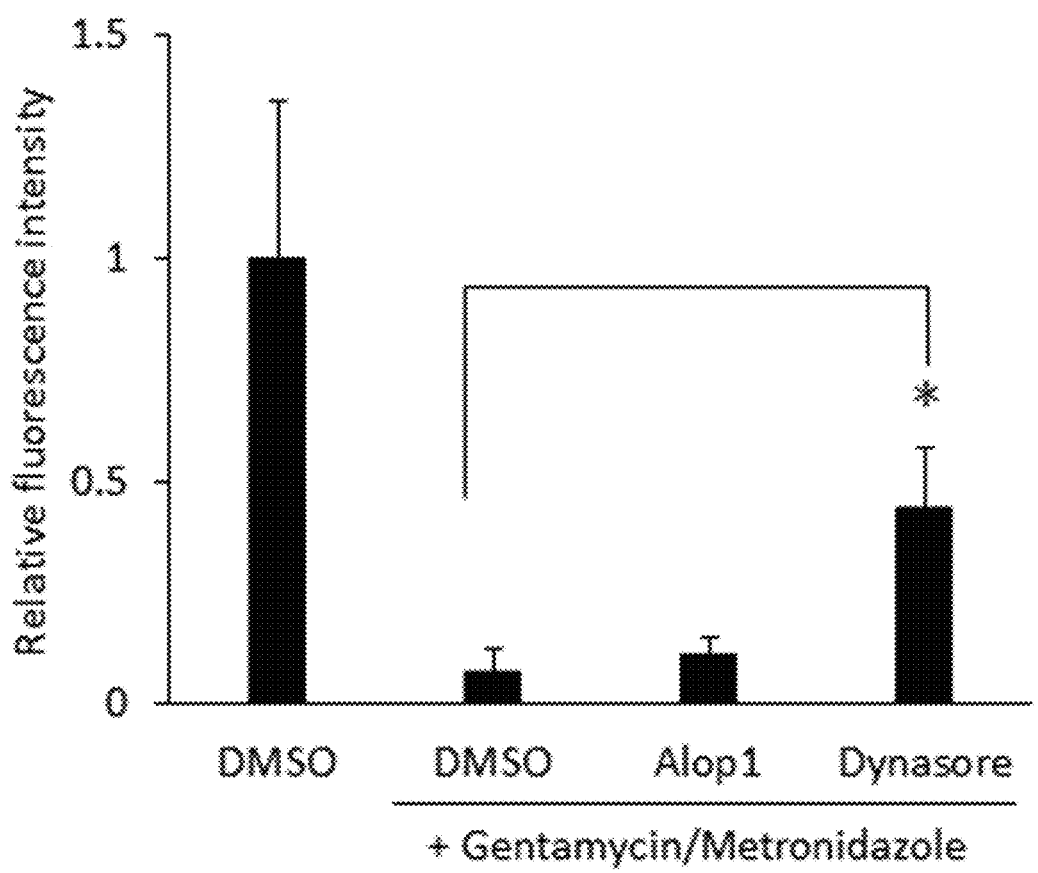

Dynasore is a well-known a cell-permeable inhibitor of dynamin, a GTPase protein [26]. Therefore, it was speculated that besides having an inhibitory effect on endocytosis, dynasore may also block *P. gingivalis* from spreading among host cells. Exit of intracellular *P. gingivalis* 33277 from HOKs was examined using immunofluorescence confocal microscopy. HOKs with intracellular *P. gingivalis* cells were cultured in the presence of 30 μMAlop1 or dynasore as well as antibiotics including gentamicin and metronidazole for 20 h. It is presumed that *P. gingivalis* cells exiting from HOKs would be eliminated by antibiotics, leading to a decrease in the number of intracellular bacteria. As expected, fewer *P. gingivalis* cells were detected in HOKs in the presence of antibiotics compared to those in HOKs not exposed to antibiotics (FIGS. 6A and 6B). This result indicates a cell entry, exit, and reentry cycle of *P. gingivalis*. Decreased intracellular *P. gingivalis* was also observed in HOKs treated with Alop1 and antibiotics, indicating that Alop1 did not affect the exit of *P. gingivalis* from HOKs. However, no significant change in the fluorescence intensity reflects the number of intracellular *P. gingivalis* in the presence or absence of dynasore, suggesting that dynasore may be involved in blocking intracellular bacterial exit.

Effect of Alop1 and Dynasore on *P. gingivalis* Phenotypes

Figure 7A:
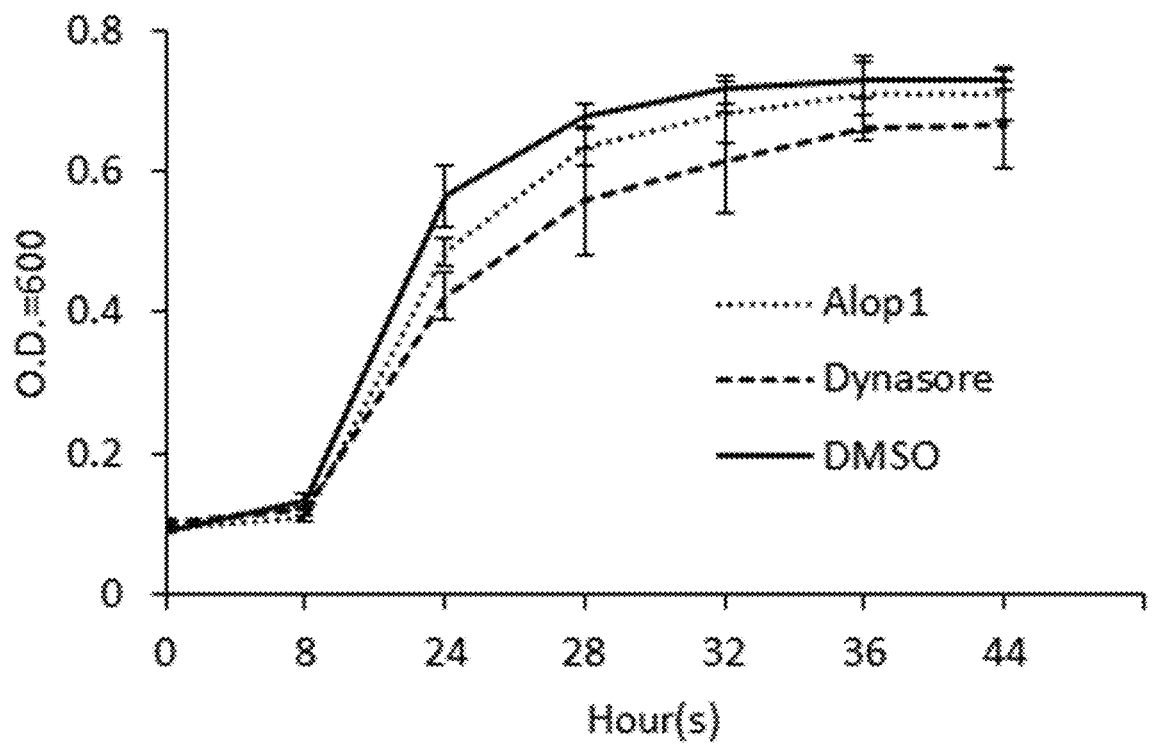
FIGS. 7A and 7B. Effects of Alop1 and dynasore on bacterial growth and gene expression in *P. gingivalis*.
Figure 7B:
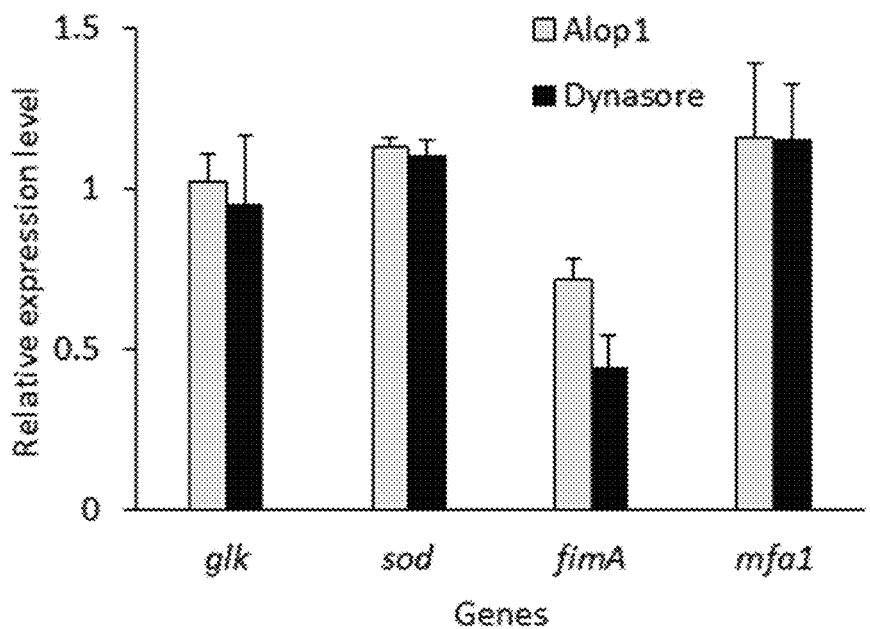

To determine if Alop1 and dynasore have any effect on phe notypes of *P. gingivalis*, the bacterial growth rate and expression level of adhesins was tested. The results showed similar patterns of the growth kinetics when *P. gingivalis* was cultured in TSB supplemented with or without 30 μMAlop1 or dynasore for a period of 44 h (FIG. 7A). Interestingly, both Alop1 and dynasore specifically inhibited expression of fimA, a gene encoding a major subunit of the long fimbriae of *P. gingivalis* (FIG. 7B). The major fimbriae are necessary for *P. gingivalis* attachment to oral surfaces and co-adhesion with other oral bacteria. Regulation of fimA expression by the compounds might be an additional mechanism to inhibit *P. gingivalis* entry.

Discussion

Invasion into host cells is an important feature of opportunistic bacterial pathogens, enabling bacteria to establish pathogenic reservoirs and evade host defense mechanisms [33,34]. *P. gingivalis*, a nonmotile organism, utilizes invasion as a major strategy to break the oral epithelial barrier and spread in periodontal tissues. The invasion process of *P. gingivalis* begins with interaction between bacteria and oral epithelial cells, followed by cytoskeleton-associated internalization [15]. Effective inhibitory agents directly targeting *P. gingivalis* invasion have not been reported. This study tested two small molecules, Alop-1 and dynasore, for their potential role in inhibition of *P. gingivalis* invasion. The results demonstrated that both compounds inhibit *P. gingivalis* invasion. Dynasore is a well-known inhibitor of dynamin, essential for clathrin-coated vesicle formation and pinch-off in endocytosis [26,35,36]. Therefore, this work confirms the involvement of endocytosis in internalization of *P. gingivalis*, which was suggested from previous observations of the co-localization of intracellular *P. gingivalis* cells and an early endosome marker (EEA1) and the rearrangement of cytoskeleton using microscopic analyses [37, 38]. Previously, Duncan et al. also suggested that *P. gingivalis* invasion may depend on a clathrin-mediated endocytosis based on the finding that a binding domain of gingipains interacted with clathrin of epithelial cells [39]. This study further explicates that, of all the endocytic pathways, clathrin-mediated endocytosis is responsible for invasion of oral epithelial cells by *P. gingivalis* and its outer membrane vesicles. In contrast to dynasore, the biological mechanism(s) of Alop1 is not well studied, despite previous reports of its various biological activities [22,23,40]. The role of Alop1 in microtubule arrangement revealed in this work suggests a possible mechanism of action that may account for its inhibitory activity of the bacterial entry.

Besides its role in clathrin-coated vesicle formation in endocytosis, dynamin is also involved in trafficking of these vesicles in the cells [35,41]. Therefore, this study tested if dynasore can inhibit cell-cell spreading of *P. gingivalis* through restraining intracellular movement of clathrincoated vesicles, since it has been suggested that entry and exit of *P. gingivalis* from host cells involves an endocytic recycling pathway [42]. As expected, dynasore was able to block the bacterial exit from HOKs. Dynasore's pleiotropic effects on inhibition of *P. gingivalis* entering oral epithelial cells and on prevention of the intracellular bacteria spreading make it a good anti-*P. gingivalis* candidate. The dual activities could efficiently eliminate *P. gingivalis* infection of oral mucosa, as super-layers constantly cast off from the epithelial surface, thus in the presence of dynasore the bacteria would not be able to reach into deep tissues.

Notably, this study also observed significantly differential rearrangement of the microtubule cytoskeleton in HOKs treated with Alop1 and dynasore compared to untreated cells. The rearrangement of microtubules induced by these two compounds led to different morphologies, suggesting that Alop1 and dynasore may target distinct events of the microtubule arrangement. Unlike most invasive microbes that utilize the actin cytoskeleton for their entry into host cells, only a few bacteria, including *P. gingivalis*, are reported to exploit the microtubule network for their internalization [21,43]. Although these data have not provided a mechanism of Alop1 or dynasore action on microtubule, a potential link between these compounds and microtubule arrangement has been established. It was previously reported that dynamin α-tubulin and γ-tubulin are immuneprecipitated with the middle domain of dynamin, which might play a role in centrosome cohesion [44]. Thus, it is reasonable to assume that dynasore, as a dynamin inhibitor, promotes centrosome splitting and prevents microtubulin nucleation in HOKs; the latter was indeed observed in this study. It should be pointed out that although dynasore is known to block the entry of several viruses including herpes simplex virus [45], it has not been considered for systemic administration as an anti-infective pharmacological agent, mainly because of the role of dynamin in broad biological functions such as neuronal transmission [41]. However, local delivery of antimicrobial agents using fiber, chip, gel, and microspheres has been recommended as a statistically and clinically significant option in the treatment of chronic periodontitis [46]. Therefore, the application of Alop1 and dynasore for elimination of *P. gingivalis* infection may provide an opportunity for the treatment of periodontitis.

References

1. Lamont R J, Jenkinson H F (1998) Life below the gum line: pathogenic mechanisms of *Porphyromonas gingivalis*. Microbiol Mol Biol Rev 62: 1244-1263. PMID: 9841671. 2. Ximenez-Fyvie L A, Haffajee A D, Socransky S S (2000) Comparison of the microbiota of supra- and subgingival plaque in health and periodontitis. J Clin Periodontol 27: 648-657. PMID: 10983598. 3. Hajishengallis G, Darveau R P, Curtis M A (2012) The keystone-pathogen hypothesis. Nat Rev Microbiol 10: 717-725. doi: 10.1038/nrmicro2873 PMID: 22941505. 4. Hajishengallis G, Liang S, Payne M A, Hashim A, Jotwani R, Eskan M A, et al. (2011) Low-abundance biofilm species orchestrates inflammatory periodontal disease through the commensal microbiota and complement. Cell Host Microbe 10: 497-506. doi: 10.1016/j.chom.2011.10.006 PMID: 22036469. 5. Zenobia C, Hajishengallis G (2015) *Porphyromonas gingivalis* virulence factors involved in subversion of leukocytes and microbial dysbiosis. Virulence 6: 236-243. doi: 10.1080/21505594.2014.999567 PMID: 25654623. 6. Lamont R J, Jenkinson H F (2000) Subgingival colonization by *Porphyromonas gingivalis*. Oral Microbiol Immunol 15: 341-349. PMID: 11154429 7. Kolenbrander P E (2000) Oral microbial communities: biofilms, interactions, and genetic systems. Annu Rev Microbiol 54: 413-437. PMID: 11018133. 8. Lamont R J, Yilmaz O (2002) In or out: the invasiveness of oral bacteria. Periodontol 2000 30: 61-69. 9. Deshpande R G, Khan M B, Genco C A (1998) Invasion of aortic and heart endothelial cells by *Porphyromonas gingivalis*. Infect Immun 66: 5337-5343. PMID: 9784541. 10. Chaudhuri S, Pratap S, Paromov V, Li Z, Mantri C K, Xie H (2014) Identification of a diguanylate cyclase. and its role in *Porphyromonas gingivalis* virulence. Infect Immun 82: 2728-2735. doi: 10.1128/IAI. 00084-14 PMID: 24733094. 11. Yilmaz O, Watanabe K, Lamont R J (2002) Involvement of integrins in fimbriae-mediated binding and invasion by *Porphyromonas gingivalis*. Cell Microbiol 4: 305-314. PMID: 12027958. 12. Dorn B R, Harris U, Wujick C T, Vertucci F J, Progulske-Fox A (2002) Invasion of vascular cells in vitro by *Porphyromonas endodontalis*. Int Endod J 35: 366-371. PMID: 12059938. 13. Li L, Michel R, Cohen J, Decarlo A, Kozarov E (2008) Intracellular survival and vascular cell-to-cell transmission of *Porphyromonas gingivalis*. BMC Microbiol 8: 26. doi: 10.1186/1471-2180-8-26 PMID: 18254977. 14. Madianos P N, Papapanou P N, Nannmark U, Dahlen G, Sandros J (1996) *Porphyromonas gingivalis* FDC381 multiplies and persists within human oral epithelial cells in vitro. Infect Immun 64: 660-664. PMID: 8550223. 15. Tribble G D, Lamont R J (2010) Bacterial invasion of epithelial cells and spreading in periodontal tissue. Periodontol 2000 52: 68-83. 16. Amar S, Wu S C, Madan M (2009) Is *Porphyromonas gingivalis* cell invasion required for atherogenesis? Pharmacotherapeutic implications. J Immunol 182: 1584-1592. PMID: 19155507. 17. Ho M H, Chen C H, Goodwin J S, Wang B Y, Xie H (2015) Functional Advantages of *Porphyromonas gingivalis* Vesicles. PLoS One 10: e0123448. doi: 10.1371/journal.pone.0123448 PMID: 25897780. 18. Mantri C K, Chen C H, Dong X, Goodwin J S, Pratap S, Paromov V, et al. (2015) Fimbriae-mediated outer membrane vesicle production and invasion of *Porphyromonas gingivalis*. Microbiologyopen 4: 53-65. doi: 10.1002/mbo3.221 PMID: 25524808. 19. Nakagawa I, Amano A, Inaba H, Kawai S, Hamada S (2005) Inhibitory effects of *Porphyromonas gingivalis* fimbriae on interactions between extracellular matrix proteins and cellular integrins. Microbes Infect 7: 157-163. PMID: 15716056. 20. Yilmaz O, Young P A, Lamont R J, Kenny G E (2003) Gingival epithelial cell signalling and cytoskeletal responses to *Porphyromonas gingivalis* invasion. Microbiology 149: 2417-2426. PMID: 12949167 21. Lamont R J, Chan A, Belton C M, Izutsu K T, Vasel D, Weinberg A (1995) *Porphyromonas gingivalis* invasion of gingival epithelial cells. Infect Immun 63: 3878-3885. PMID: 7558295. 22. Dang Z, Jung K, Zhu L, Lai W, Xie H, Lee K H, et al. (2014) Identification and synthesis of quinolizidines with anti-influenza a virus activity. ACS Med Chem Lett 5: 942-946. doi: 10.1021/ml500236n PMID: 25147619. 23. Wang H, Yang S, Zhou H, Sun M, Du L, Wei M, et al. (2015) Aloperine executes antitumor effects against multiple myeloma through dual apoptotic mechanisms. J Hematol Oncol 8: 26. doi: 10.1186/s13045-015-0120-x PMID: 25886453. 24. Zhou C C, Gao H B, Sun X B, Shi H B, Liu W, Yuan H N, et al. (1989) Anti-inflammatory and anti-allergic action of aloperine. Zhongguo Yao Li Xue Bao 10: 360-365. PMID: 2533795. 25. Chu V C, Whittaker G R (2004) Influenza virus entry and infection require host cell N-linked glycoprotein. Proc Natl Acad Sci USA 101: 18153-18158. PMID: 15601777. 26. Macia E, Ehrlich M, Massol R, Boucrot E, Brunner C, Kirchhausen T (2006) Dynasore, a cell-permeable inhibitor of dynamin. Dev Cell 10: 839-850. PMID: 16740485. 27. Furuta N, Tsuda K, Omori H, Yoshimori T, Yoshimura F, Amano A (2009) *Porphyromonas gingivalis* outer membrane vesicles enter human epithelial cells via an endocytic pathway and are sorted to lysosomal compartments. Infect Immun 77: 4187-4196. doi: 10.1128/IA1.00009-09 PMID: 19651865. 28. Kulp A, Kuehn M J (2010) Biological functions and biogenesis of secreted bacterial outer membrane vesicles. Annu Rev Microbiol 64: 163-184. doi: 10.1146/annurev.micro.091208.073413 PMID: 20825345. 29. Macdonald I A, Kuehn M J (2013) Stress-induced outer membrane vesicle production by *Pseudomonas. aeruginosa*. J Bacteriol 195: 2971-2981. doi: 10.1128/J13.02267-12 PMID: 23625841. 30. Radhakrishnan G K, Splitter G A (2012) Modulation of host microtubule dynamics by pathogenic bacteria. Biomol Concepts 3: 571-580. PMID: 23585820. 31. Moffatt C E, Inaba H, Hirano T, Lamont R J (2012) *Porphyromonas gingivalis* SerB-mediated dephosphorylation of host cell cofilin modulates invasion efficiency. Cell Microbiol 14: 577-588. doi: 10.1111/j. 1462-5822.2011.01743.x PMID: 22212282. 32. Tribble G D, Mao S, James C E, Lamont R J (2006) A *Porphyromonas gingivalis* haloacid dehalogenase family phosphatase interacts with human phosphoproteins and is important for invasion. Proc Natl Acad Sci USA 103: 11027-11032. PMID: 16832066. 33. Foster T J, Geoghegan J A, Ganesh V K, HookM (2014) Adhesion, invasion and evasion: the many functions of the surface proteins of *Staphylococcus aureus*. Nat Rev Microbiol 12: 49-62. doi: 10.1038/nrmicro3161 PMID: 24336184. 34. Hunstad D A, Justice S S (2010) Intracellular lifestyles and immune evasion strategies of uropathogenic *Escherichia coli*. Annu Rev Microbiol 64: 203-221. doi: 10.1146/annurev.micro.112408.134258 PMID: 20825346. 35. Abazeed M E, Blanchette J M, Fuller R S (2005) Cell-free transport from the trans-golgi network to late endosome requires factors involved in formation and consumption of clathrin-coated vesicles. J Biol Chem 280: 4442-4450. PMID: 15572353. 36. Danino D, Moon K H, Hinshaw J E (2004) Rapid constriction of lipid bilayers by the mechanochemical enzyme dynamin. J Struct Biol 147: 259-267. PMID: 15450295. 37. Belton C M, Izutsu K T, Goodwin P C, Park Y, Lamont R J (1999) Fluorescence image analysis of the association between *Porphyromonas gingivalis* and gingival epithelial cells. Cell Microbiol 1: 215-223. PMID: 11207554. 38. Takeuchi H, Furuta N, Morisaki I, Amano A (2011) Exit of intracellular *Porphyromonas gingivalis* from gingival epithelial cells is mediated by endocytic recycling pathway. Cell Microbiol 13: 677-691. doi: 10.1111/j.1462-5822.2010.01564.x PMID: 21155963. 39. Boisvert H, Duncan M J (2008) Clathrin-dependent entry of a gingipain adhesin peptide and *Porphyromonas gingivalis* into host cells. Cell Microbiol 10: 2538-2552. doi: 10.1111/j.1462-5822.2008.01228.x PMID: 18717820. 40. Lin W C, Lin J Y (2011) Five bitter compounds display different anti-inflammatory effects through modulating cytokine secretion using mouse primary splenocytes in vitro. J Agric Food Chem 59: 184-192. doi: 10.1021/jf103581r PMID: 21155568. 41. Robinson M S (2015) Forty Years of Clathrin-coated Vesicles. Traffic. 16: 1210-38. doi: 10.1111/tra.12335 PMID: 26403691. 42. Takeuchi H, Furuta N, Amano A (2011) Cell entry and exit by periodontal pathogen via recycling pathway. Commun Integr Biol 4: 587-589. doi: 10.4161/cib.4.5.16549 PMID: 22046471. 43. Yoshida S, Sasakawa C (2003) Exploiting host microtubule dynamics: a new aspect of bacterial invasion. Trends Microbiol 11: 139-143. PMID: 12648946. 44. Thompson H M, Cao H, Chen J, Euteneuer U, McNiven M A (2004) Dynamin 2 binds gamma-tubulin and participates in centrosome cohesion. Nat Cell Biol 6: 335-342. PMID: 15048127. 45. Mues M B, Cheshenko N, Wilson D W, Gunther-Cummins L, Herold B C (2015) Dynasore disrupts trafficking of herpes simplex virus proteins. J Virol 89: 6673-6684. doi: 10.1128/JVI.00636-15 PMID: 25878109. 46. Killoy W J (2002) The clinical significance of local chemotherapies. J Clin Periodontol 29 Suppl 2: 22-29.

H. Conclusions

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

What is claimed:

1. A method of treating or reducing the likelihood of periodontitis, a periodontitis-related condition, or a periodontitis-related symptom in a subject in need thereof, comprising:
   locally administering to the subject a therapeutically effective amount of a compound selected from the group consisting of: an inhibitor of vesical formation, an inhibitor of endocytosis, an inhibitor of dynamin, and combinations thereof.

2. The method of claim 1, wherein the locally administering comprises locally administering to gingival tissue of the subject.

3. The method of claim 1, wherein the compound comprises dynasore or a pharmaceutically acceptable salt thereof.

4. The method of claim 3, wherein the dynasore or pharmaceutically acceptable salt thereof is administered in a composition containing from 1.2 µM to 30 µM of said dynasore or a pharmaceutically acceptable salt thereof.

5. The method of claim 1, wherein the compound comprises aloperine or a pharmaceutically acceptable salt thereof.

6. The method of claim 5, wherein the aloperine or a pharmaceutically acceptable salt thereof is administered in a composition containing from 6 µM to 30 µM of said aloperine or a pharmaceutically acceptable salt thereof.

7. The method of claim 5, wherein the aloperine or a pharmaceutically acceptable salt thereof is administered in an amount of up to 869 mg/kg of the subject.

8. The method of claim 1, wherein the compound is dynasore, and wherein the therapeutically effective amount is sufficient to achieve a minimum concentration in gingival tissue of the subject, and wherein the minimum concentration is selected from the group consisting of: 12 nM, 120 nM, 1.2 µM, 6 µM, and 30 µM.

9. The method of claim 1, wherein the compound is aloperine, and wherein the therapeutically effective amount is sufficient to achieve a minimum concentration in gingival tissue of the subject, and wherein the minimum concentration is selected from the group consisting of: 60 nM, 600 nM, 6 µM, and 30 µM.

10. The method of claim 1, wherein the subject suffers from or is at risk of an infection of *Porphyromonas gingivalis*.

11. The method of claim 1, wherein the compound is administered in a dentifrice selected from the group consisting of: a paste, a gel, a mouthwash, a powder, and a tooth soap.

12. The method of claim 1, wherein the therapeutically effective amount of the compound is administered with a pharmaceutically acceptable carrier.

13. The method of claim 1, wherein the therapeutically effective amount is sufficient to achieve a concentration of at least 6 µM of the compound in gingival tissue of the subject.

14. The method of claim 1, wherein the therapeutically effective amount is sufficient to achieve a concentration of at least 30 µM of the compound in gingival tissue of the subject.

15. The method of claim 1, wherein the periodontitis, periodontitis-related condition, or periodontitis-related symptom is bacterial mediated.

16. The method of claim 1, wherein the periodontitis, periodontitis-related condition, or periodontitis-related symptom is mediated by *Porphyromonas gingivalis*.

17. The method of claim 1, wherein the compound is aloperine, and wherein the therapeutically effective amount is up to the median lethal dose (LD50) of aloperine.

18. The method of claim 1, wherein the compound is dynasore, and wherein the therapeutically effective amount is up to the median lethal dose (LD50) of dynasore.

* * * * *